US010556109B2

United States Patent
Lopez-Poveda

(10) Patent No.: US 10,556,109 B2
(45) Date of Patent: Feb. 11, 2020

(54) SOUND ENHANCEMENT FOR COCHLEAR IMPLANTS

(71) Applicant: UNIVERSIDAD DE SALAMANCA, Salamanca (ES)

(72) Inventor: Enrique Alejandro Lopez-Poveda, Salamanca (ES)

(73) Assignee: UNIVERSIDAD DE SALAMANCA (ES)

( * ) Notice: Subject to any disclaimer, the term of this patent is extended or adjusted under 35 U.S.C. 154(b) by 0 days.

(21) Appl. No.: 15/303,798

(22) PCT Filed: Apr. 28, 2015

(86) PCT No.: PCT/EP2015/059230
§ 371 (c)(1),
(2) Date: Oct. 13, 2016

(87) PCT Pub. No.: WO2015/169649
PCT Pub. Date: Nov. 12, 2015

(65) Prior Publication Data
US 2017/0043162 A1 Feb. 16, 2017

(30) Foreign Application Priority Data
May 8, 2014 (EP) .................................. 14167487

(51) Int. Cl.
*A61N 1/36* (2006.01)
*H04R 25/00* (2006.01)

(52) U.S. Cl.
CPC ....... *A61N 1/36032* (2013.01); *H04R 25/356* (2013.01); *H04R 25/552* (2013.01)

(58) Field of Classification Search
CPC ............ A61N 1/36036; A61N 1/36032; A61N 1/0541; H04R 25/70; H04R 25/554;
(Continued)

(56) References Cited

U.S. PATENT DOCUMENTS

2004/0172101 A1  9/2004  Van Hoesel
2004/0190734 A1  9/2004  Kates
(Continued)

FOREIGN PATENT DOCUMENTS

WO  2010022456 A1  3/2010
WO  2013164511 A1  11/2013

OTHER PUBLICATIONS

Wilson et al., "Better Speech Recognition with Cochlear Implants", Letters to Nature, Jul. 18, 1991, pp. 236-238, vol. 352, Nature.
(Continued)

*Primary Examiner* — William J Levicky
*Assistant Examiner* — Minh Duc G Pham
(74) *Attorney, Agent, or Firm* — Hayes Soloway PC

(57) ABSTRACT

This document mainly discloses a method and a device for sound enhancement, both aspects of the invention hereby described are directed to cochlear implants. The method for sound enhancement and the sound enhancement device comprising a component adapted to carry out said method are based on processing the envelope for frequency bands of the acoustic signal captured, said amplification is directed to the gain value of the amplification according to an amplitude of an output signal of the other sound processor.

15 Claims, 26 Drawing Sheets

(58) Field of Classification Search
CPC .. H04R 25/505; H04R 25/356; H04R 25/552; H04R 2225/43; H04R 2225/67
USPC .......................................................... 607/57
See application file for complete search history.

(56) References Cited

U.S. PATENT DOCUMENTS

| | | |
|---|---|---|
| 2009/0304188 A1 | 12/2009 | Mejia et al. |
| 2012/0008809 A1* | 1/2012 | Vandali ............... G10L 21/0205 381/317 |
| 2012/0093329 A1 | 4/2012 | Francart et al. |
| 2013/0010973 A1* | 1/2013 | Ma ....................... H04R 25/356 381/23.1 |

OTHER PUBLICATIONS

Wilson et al., "Two New Directions in Speech Processor Design for Cochlear Implants", Ear & Hearing, Aug. 2005, pp. 73S-81S, vol. 26, Issue 4, the Official Journal of the American Auditory Society.
Wiggins et al., "Linking Dynamic-Range Compression Across the Ears Can Improve Speech Intelligibility in Spatially Separated Noise", Feb. 2013, pp. 1004-1016, Acoustical Society of America.
Wilson et al., "Possibilities for a Closer Mimicking of Normal Auditory Functions with Cochlear Implants", 2006, pp. 48-56, Thieme Medical Publishers, New York.
Wilson et al., "Use of Auditory Models in Developing Coding Strategies for Cochlear Implants", 2010, pp. 237-260, Springer-Verlag, New York.
Schatzer, "Novel Concepts for Stimulation Strategies in Cochlear Implants", 2010, University of Innsbruck, Germany.

* cited by examiner

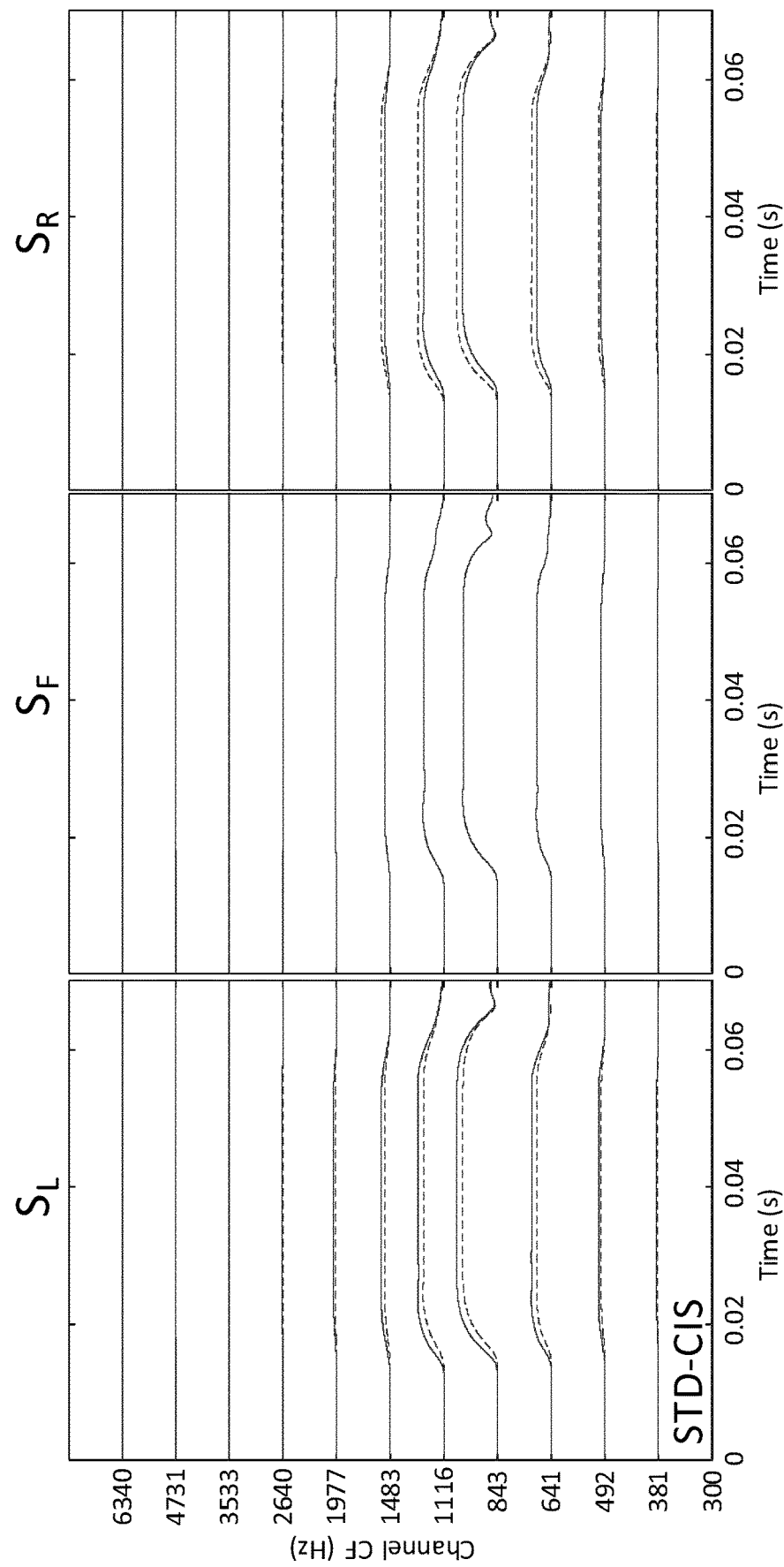

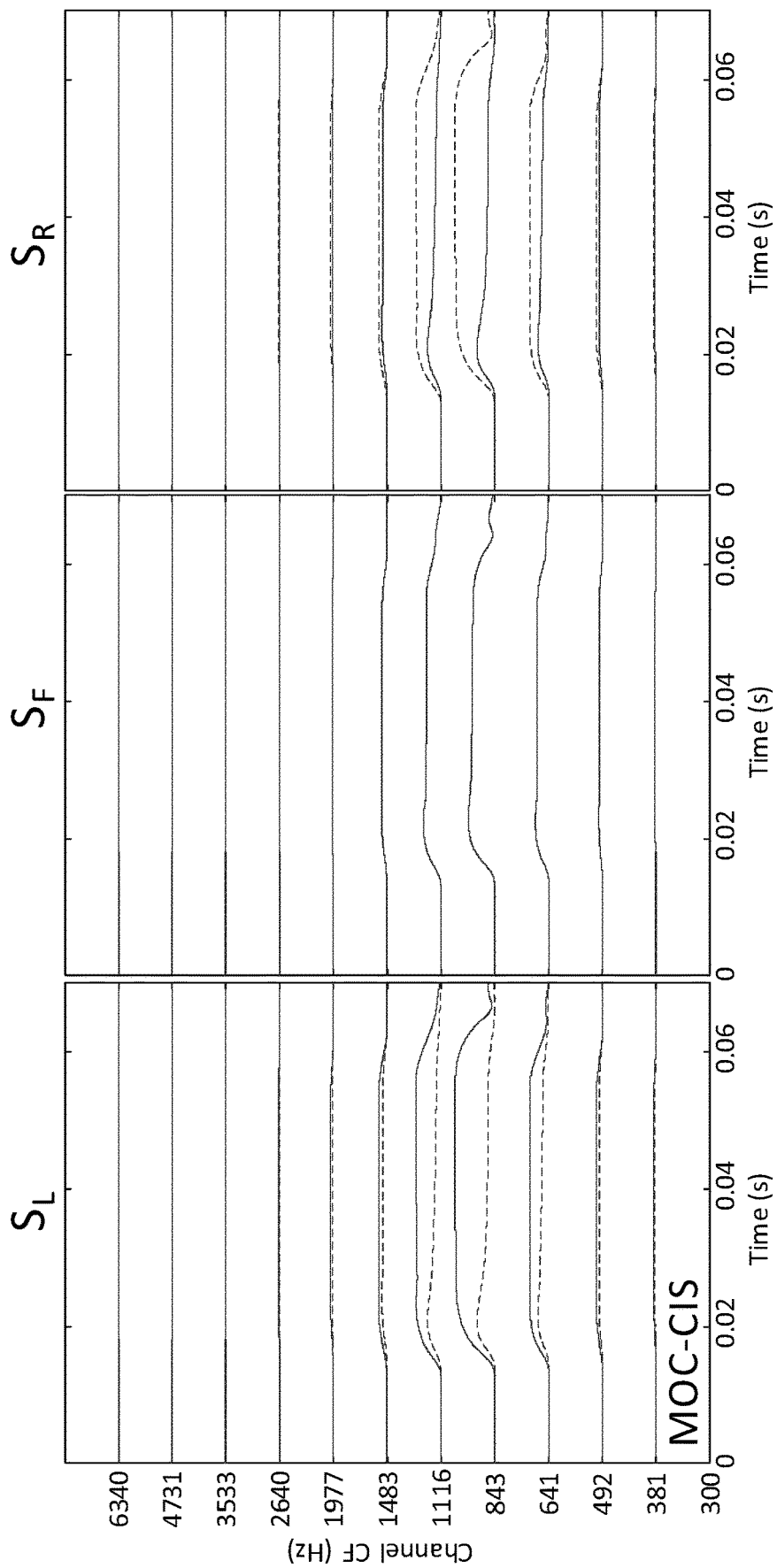

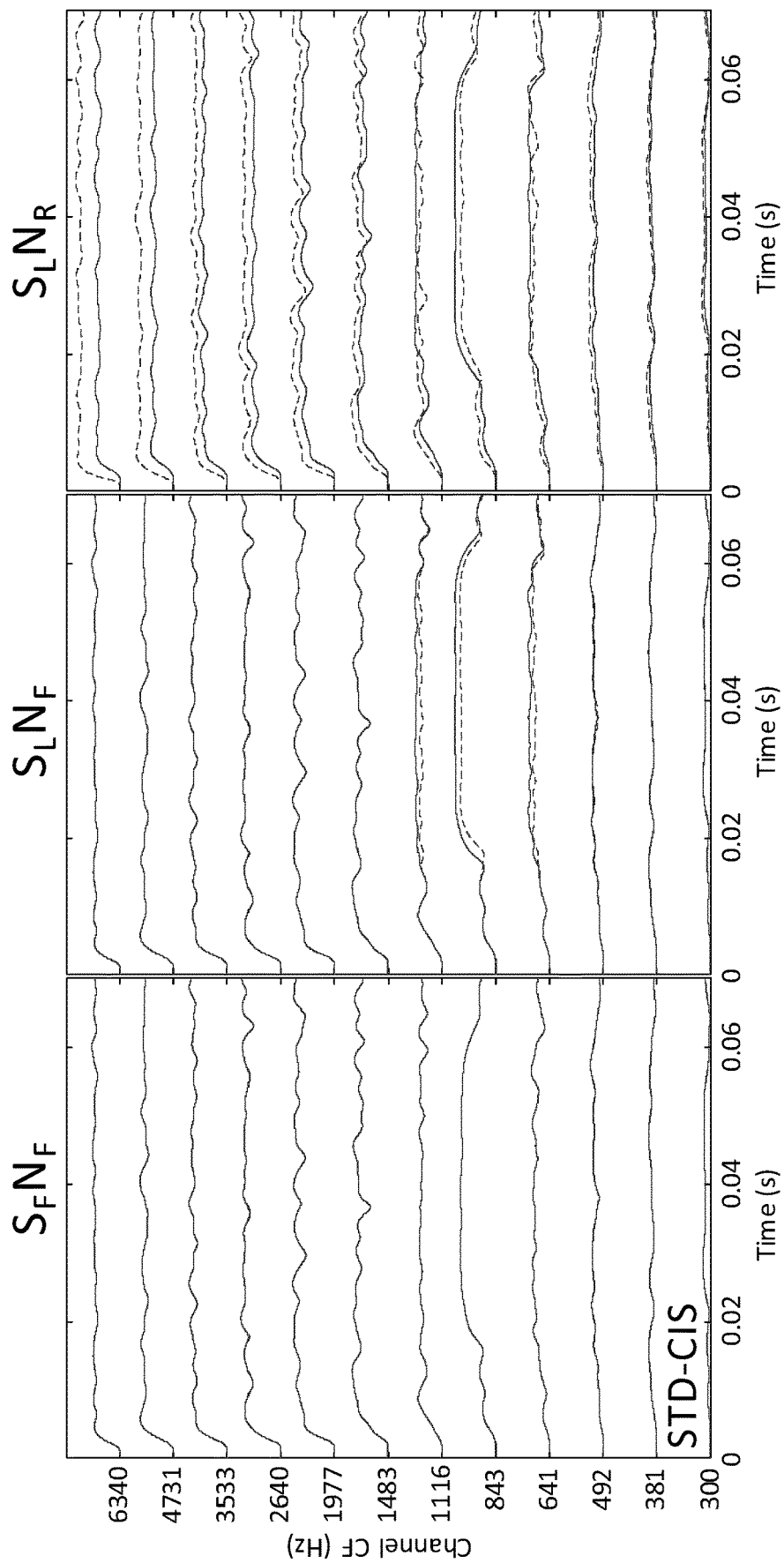

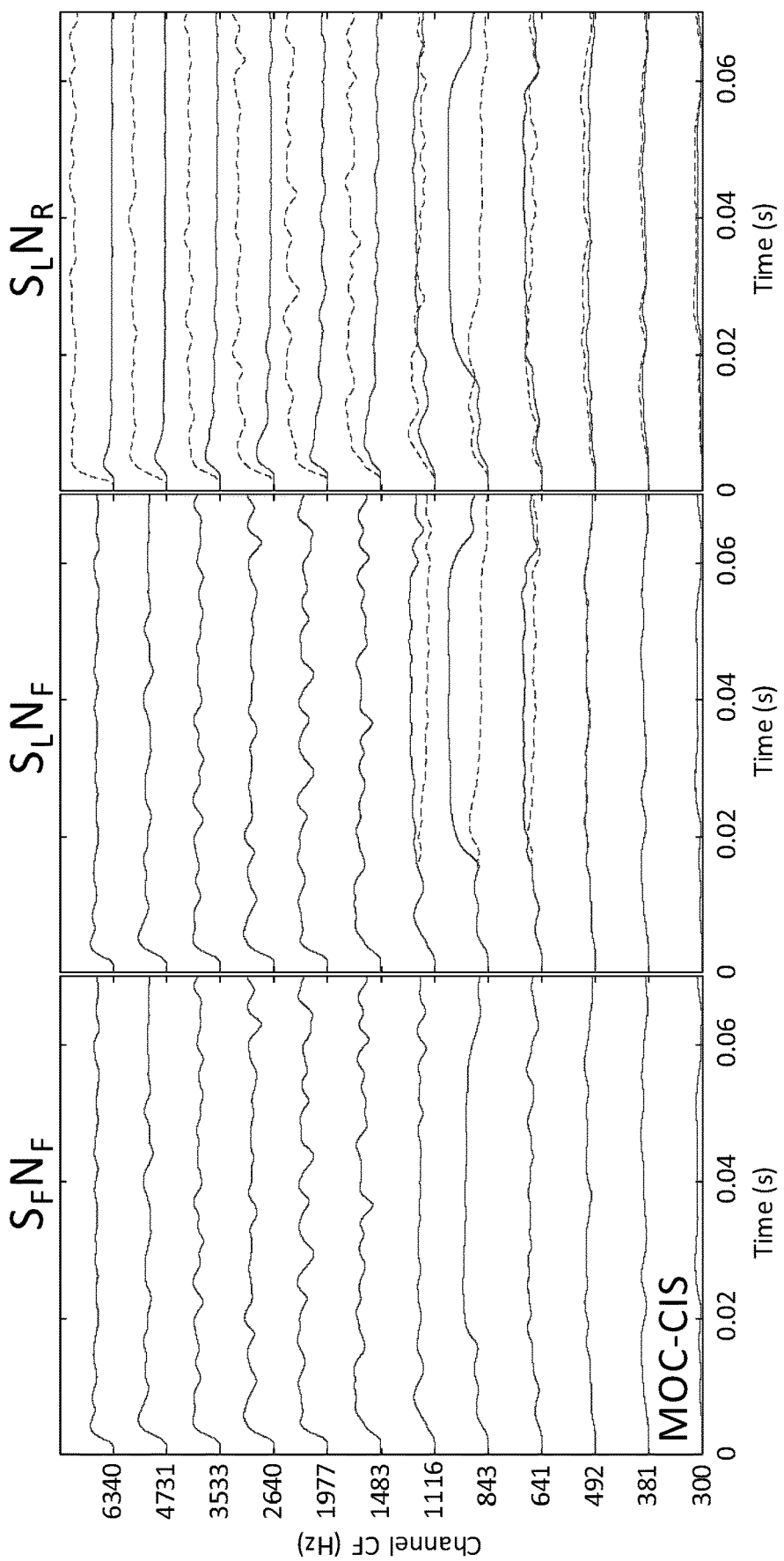

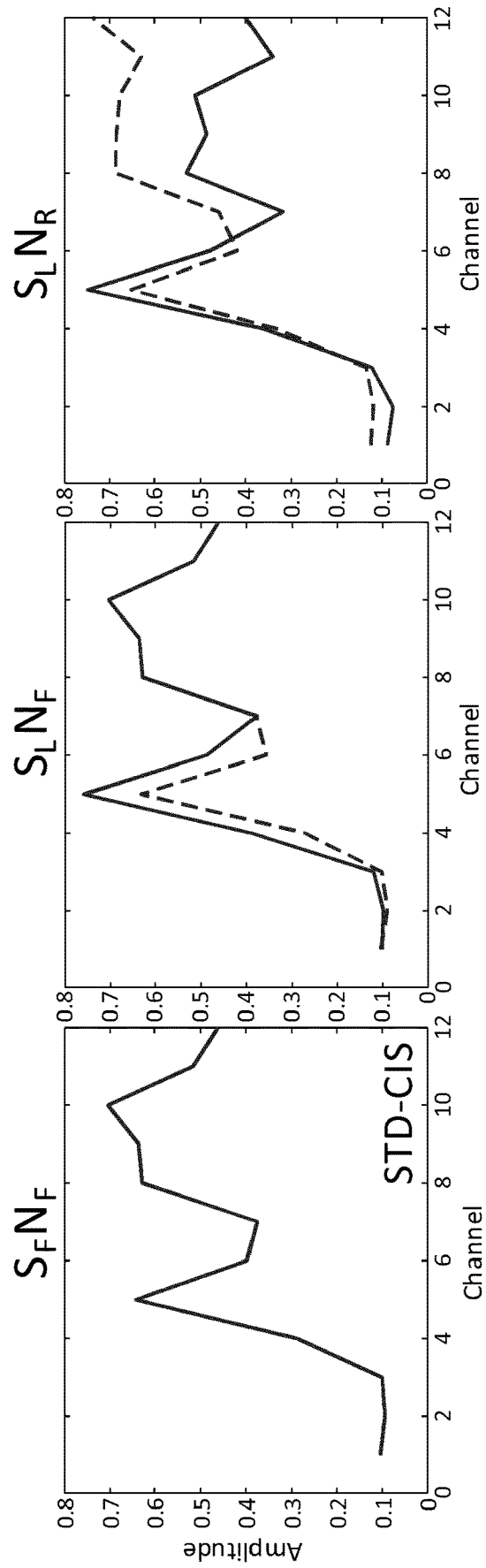

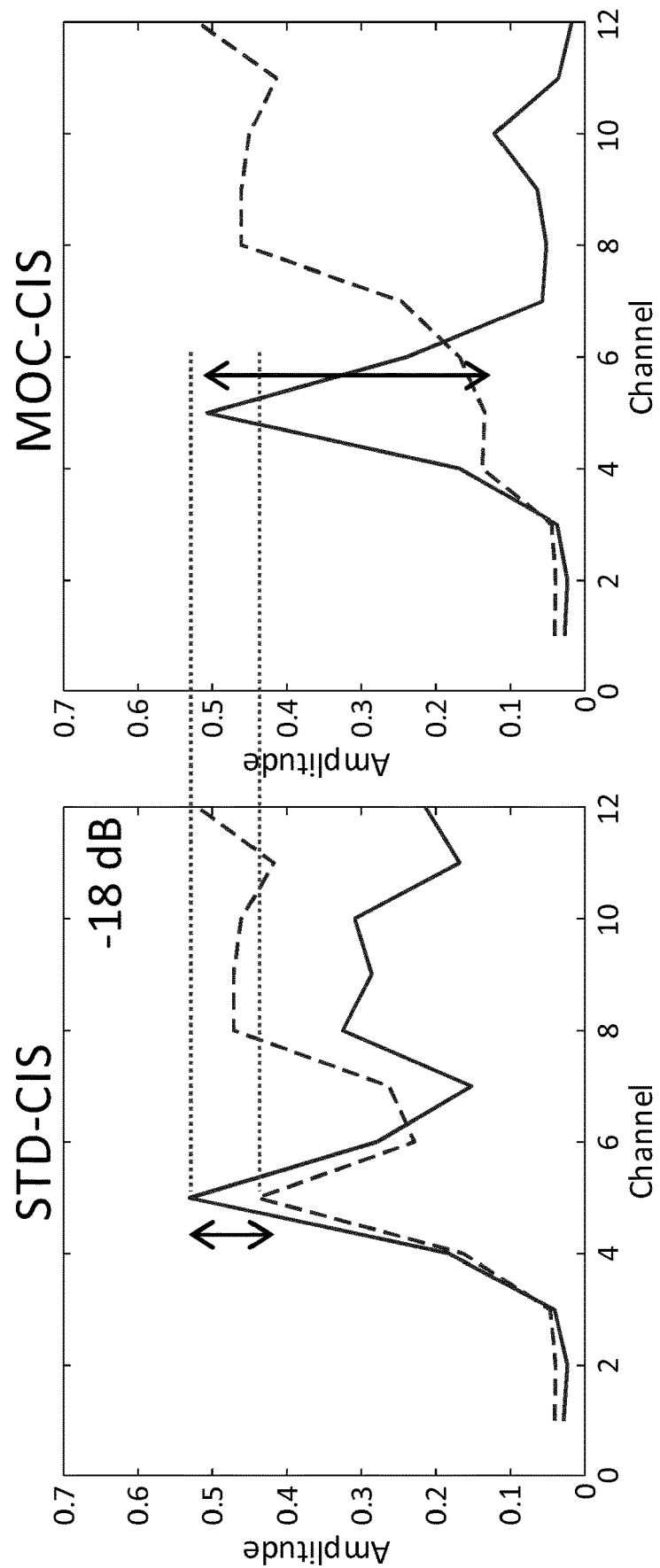

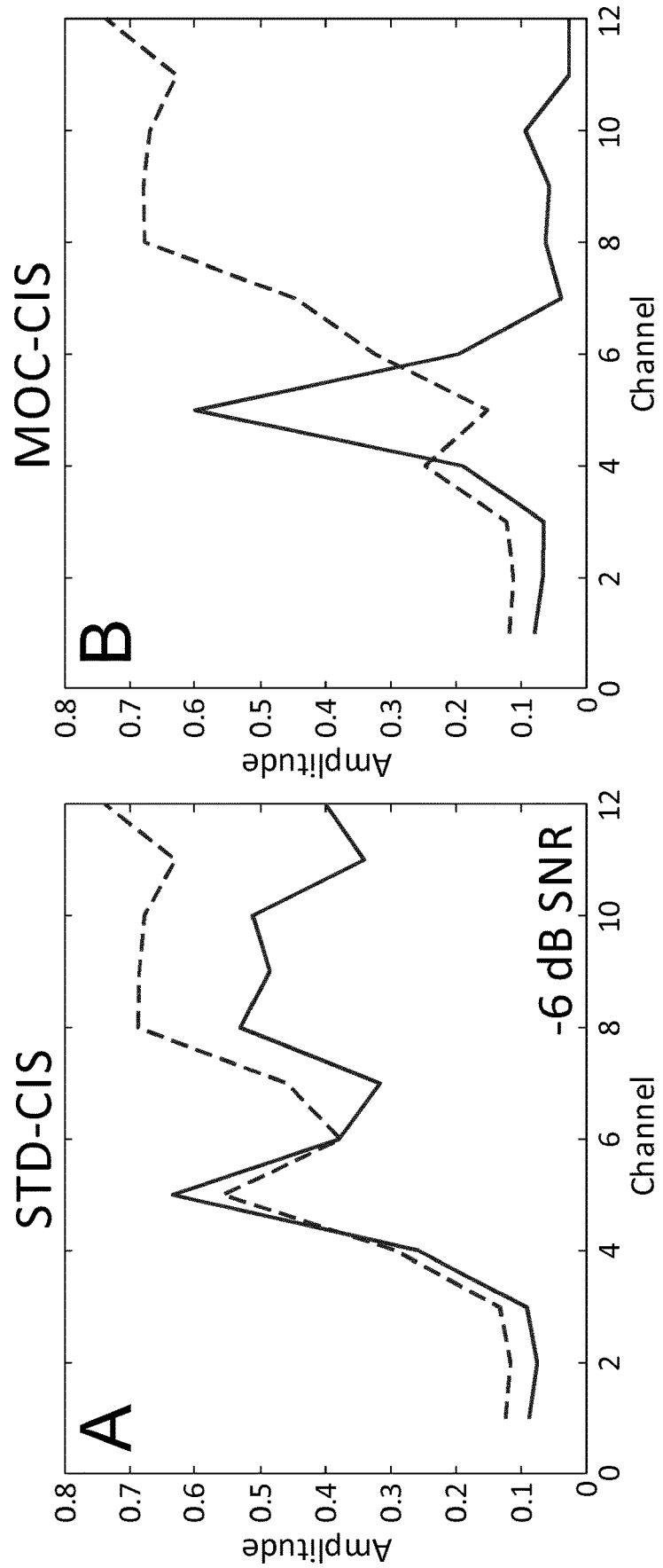

−0 dB SNR

SOUND ENHANCEMENT FOR COCHLEAR IMPLANTS

OBJECT OF THE INVENTION

The present invention belongs to the field of systems and methods for sound processing.

The main object of the present invention is a binaural sound processing method for cochlear implants allowing enhancement of sound in noisy environments.

BACKGROUND OF THE INVENTION

At present, different types of implantable hearing prostheses are available for cases of total or partial hearing loss. Said devices are based on principles of electromagnetic, mechanical, piezoelectric or electric actuation.

The cochlear implant is a hearing prosthesis capable of restoring hearing in deaf people or people with hypoacusis, whose auditory nerve remains functional. More specifically a cochlear implant is based on a transducer which transforms the acoustic signals picked up by a microphone in electrical signals that stimulate the auditory nerve.

A fundamental element of the cochlear implant is the "sound processor", which determines the electrical stimulation pattern which will be delivered through the electrodes of the implant. Said stimulation pattern varies according to the sound conditions of each situation. Furthermore, the electrodes are introduced in the scaly tympani of the "snail shell" or cochlea of the inner ear to finally transmit said stimuli to the auditory nerve, and from here to the brain.

The sound processors currently existing in the market aim to reproduce the information processing performed by a healthy ear. Unfortunately, said processors ignore a fundamental aspect of this processing that could be crucial for communication in noisy environments: the involuntary control over the operation of an ear exercised by the sounds received through the opposite ear (hereinafter, contra-lateral control). Perhaps for this reason, the users of cochlear implants show great difficulty for communicating in noisy environments, such as the roads and streets, premises with a lot of people such as cafeterias, bars and restaurants, etc.

In recent years, Blake S. Wilson (Duke University, USA) has led several research projects funded first by the National Institutes of Health and currently by the company MED-EL GmbH to design sound processors for cochlear implants which faithfully reproduce the operation of the healthy ear (i.e. bio-inspired systems) with the aim of improving the efficacy of the implant in noisy environments. Its solution consisted of designing a prototype of sound processor based on "computational models" of the response of the auditory nerve designed by Enrique A. Lopez-Poveda (University of Salamanca, Spain), who was incorporated in 2002 as a consultant to Blake S. Wilson's project. Reinhold Schatzer also participated in the team as engineer, currently at MED-EL Headquarters (Austria).

The operation of the bio-inspired processor and its results have been published in several documents (Wilson et al., "Two new directions in Speech Processor design for cochlear implants", 2005; "Possibilities for a closer mimicking of normal auditory functions with cochlear implants", 2006, "Use of auditory models in developing coding strategies for cochlear implants", 2010) and in the doctoral thesis doctoral of Reinhold Schatzer ("Novel concepts for stimulation strategies in cochlear implants", University of Innsbruck, 2010), but the research continues.

On the other hand, it is known that in "natural hearing", the operation of each one of the ears depends on the operation of the opposite ear, so that the brain conjugates the information that reaches it from both ears ("binaural" hearing). At this point, we should mention the existence of what is known as "bilateral cochlear implant". In this case, the user has two cochlear implants installed, one for each ear. A drawback of this type of implants is that the control and mode of operation of the implants is totally independent from one another. In other words, they lack the contra-lateral control present in healthy ears that provides the hearing to normal-hearing persons in noisy environments, hence their efficacy and performance in these noisy environments are clearly subject to improvement.

In this sense, the document US2012/0093329 uses a detection algorithm based on the inter-auricular intensity difference and processes sounds precisely on the detected inter-auricular intensity difference. This means that the sound processing technique requires from a prior detection on the intensity difference. A similar approach was disclosed by WO2010/022456A1 where the sound processing system described is also based on a detection algorithm; this detection algorithm uses a SNR signal-to-noise ratio in order to enhance the signal with respect to the noise detected. Another approach is that of US2009/0304188A1 where directional microphones are used to determine those signals considered to be relevant and perform a delay of said signals with respect of the rest of signals. All of the documents cited are based on, and therefore require, a priori detection or determination which requires more processing resources and transform signals in a way that the acoustic relevant signals may be deteriorated.

Other developments known in the art are not based on prior detection but on a time based alignment of the acoustic signals detected, in this sense the document published as US2004/0172101A1 describes a peak-derived timing stimulation strategy for a multi-channel cochlear implant, where the signals picked up by each of the two microphones are processed to align in time and Some current hearing aids (e.g., Oticon®) feature bilateral wireless synchronization to match the hearing aids' noise reduction and directionality features. They also feature binaural coordination to coordinate the volume and program changes between the two devices (i.e., to make adjustments to the two devices by adjusting just one). Oticon® claims that their binaural hearing aids preserve inter-aural differences and help the user organize the sound scene, reducing listening effort. Due to proprietary right issues, the sound processing behind these claims is unknown to the present authors. Independent scientists, however, have confirmed some of the benefits claimed by the hearing-aid manufacturer (Wiggins I M, and Seeber B U, "Linking dynamic-range compression across the ears can improve speech intelligibility in spatially separated noise", J. Acoust. Soc, Am. 133:1004-1016). Sound processing by hearing aids particularly frequency-dependent dynamic range compression, does not differ significantly from sound processing by a cochlear implant.

Therefore, the technical problem posed here is that current bilateral cochlear implants and the sound processing techniques developed do not provide an effective solution for the hearing and communication of deaf users in noisy environments, such as the streets of cities, cafeterias, etc., where there are many different sounds at the same time. This means users are not capable of understanding speech clearly, nor accurately locating and detecting the sound sources.

DESCRIPTION OF THE INVENTION

One aspect of the invention is that of sound processing method for acoustic signals, another embodiment of the invention is a sound processing device or system for sound processing of acoustic signals adapted to process sounds according to the method hereby described and yet another aspect of the invention is a cochlear implant furnished with said sound processor, yet another aspect of the invention is that of a hearing aid device implant comprising the aforementioned sound processing device.

Sound enhancement processing method for cochlear implant sound processors of the invention hereby described does not require any a-priori detection of any parameter, signal or input; the method of the invention is based on the capture of the acoustic signal by a microphone associated to a processor and a following process of that signal without any prior detection.

Unlike the abovementioned sound processing methods for bilateral cochlear implants, the sound processing method of the present invention does not involve feature (or signal) detection because no assumptions are made about the feature (or signal) of interest. The gain of a frequency channel in one device (sound processor) is inhibited in proportion to the time-weighted output amplitude from an appropriate frequency channel in the contralateral device (sound processor). As some existing sound processors described above, the sound enhancement method of the invention also enhances the SNR or the interaural sound localization cues, but this enhancement emerges naturally from its physiologically inspired functioning rather than from using feature detection and enhancement algorithms.

Since the sound processing method hereby described is based on a binaural scenario, the method requires two processors or one processor in turn emulating a second processor. Any of them, or both, may work as described since the sound process of the signal captured by each processor depends on some parameters of the other and vice versa.

So, one of the processors breaks down the incoming signal received from the microphone into frequency bands. Each frequency band is further processed in order to obtain the respective envelopes for each band, in this manner each one of the envelopes may be amplified by compression techniques.

The gain of the amplification process applied to each envelope by each processor depends on the amplitude energy of the output signal from the other processor, so the higher the output energy from one processor, the lower the amplification performed by the other processor and vice versa.

The amplified envelope is then used to modulate the amplitude of electrical pulses that may be used to stimulate the acoustic nerve when the processors are associated by means of any suitable connection. In this manner the sound processing technique hereby described may be used for cochlear implants for sound enhancement in noisy environments.

The sound enhancement processing method of the invention might comprise each of the following steps:
capturing at least an acoustic signal by means of a microphone of one of two interconnected sound processors,
breaking down the captured acoustic signal into frequency bands, by means of a sound processor,
respectively extracting for each frequency band an envelope, by means of a sound processor,
amplifying the envelope, by compression techniques, by means of the sound processor, said amplification comprising in turn modifying a gain value of the amplification according to an amplitude of an output signal from the other sound processor, wherein the relationship between the gain and the amplitude is that of the higher the energy of the amplitude of the output signal, the lower the gain of the amplification and vice versa.

Another aspect of the invention is referred to sound enhancement devices, or a specific modules of a cochlear implant sound processor operative to perform the steps required to produce a sound enhancement in cochlear implants. This aspect of the invention embraces said sound enhancement device comprising two interconnected sound processors, more precisely continuous interleaved sampling (CIS) processors, or processors of the kind known as n-of-m (e.g., Advanced Combination Encoder (ACE), Spectral Peak (SPEAK)), with respective microphones; with one of the two sound processors being adapted to process an input acoustic signal, captured by the corresponding microphone, according to an output signal from the other processor. Said sound processors are adapted to perform an amplification of the input acoustic signal by means of a gain processing of said input acoustic signal with respect to an amplitude of an output signal of the processors; this means that one of the processors works according to a signal received from the other, and vice-versa.

The sound enhancement device may present at least two configurations; a first configuration comprising two interconnected sound processors with respective microphones, sound enhancement device characterised by at least one of the two sound processors being adapted to process an input acoustic signal, captured by its corresponding microphone, according to an output signal from the other processor; a second configuration comprising at least one sound processor with at least one microphone emulating a multi processor, sound enhancement device characterized by each of the emulated sound processor being adapted to process an input acoustic signal captured by the microphone, according by the output signal from other emulated sound processor.

The sound processors may comprise at least one filter selected from: Butterworth, Bessel, Chebicheb, DRNL, and Gammachirp.

Yet another aspect of the invention is referred to a standalone cochlear implant comprising at least one module for electrical stimulation of the acoustic nerve, and a sound enhancement device adapted to carry out the sound enhancement method of the invention earlier described.

In a further aspect of the invention a hearing aid device comprising the sound enhancement device earlier described.

DESCRIPTION OF THE DRAWINGS

To complement the description being made and in order to aid towards a better understanding of the characteristics of the invention, in accordance with a preferred example of practical embodiment thereof, a set of drawings is attached as an integral part of said description wherein, with illustrative and non-limiting character, the following has been represented:

FIGS. 6a-6f. Shows a graph depicting a comparison of frequency channel outputs for two stand-alone, standard CIS processors (top) and for the two MOC-CIS processors of the invention (bottom) for a −6 dB, 1-kHz pure tone signal in quiet, for three different locations of the tone signal with respect to the listener: left (SL) (left panels), front (SF) (middle panels), and right (SR) (right panels). The tone signal had 10-ms cosine-squared onset and offset ramps, it started at 10 ms and lasted for 50 ms. Each panel illustrates the channel output amplitudes for the right-ear (red lines) and the left-ear (blue lines) processors. In each panel, each pair of blue and red lines is for a different frequency channel (12 in total).

FIG. 8a. Channel output amplitudes for the left-ear (lower line) and right-ear (upper lines) processors of the invention. The horizontal thick line illustrates the period where the stimulus was present. FIG. 8b. Instantaneous value of the compression parameter c for the left-ear (blue) and right-ear (red) processors of the invention.

FIGS. 9a-9f. Show respective graphs of a comparison of two stand-alone standard CIS processors (top) and for two processors of the invention (bottom) channel outputs for a −6 dB, 1-kHz pure tone signal in 0 dB SNR white noise, for different relative locations of the tone and the noise: signal and noise in front of the listener (SFNF) (left); signal to the left ear and noise in front of the listener (SLNF) (middle); and signal to the left ear and noise to the right ear (SLNR) (right).

FIGS. 10a-10f. Show respective graphs of a comparison of the left-ear and right-ear peak excitation patterns (at time ~37 ms) for the two stand-alone standard IS processors, one in each ear, (top panels) and for the two processors of the invention (bottom panels) for a −6 dB, 1-kHz pure tone signal in 0 dB SNR white noise for different signal-noise locations: signal and noise in front of the listener (SFNF) (left); signal to the left ear and noise in front of the listener (SLNF) (middle); and signal to the left ear and noise to the right ear (SLNR) (right).

FIGS. 11a-11d. Show respective graphs of a comparison of peak excitation patterns (at time ~37 ms) for the two standard stand-alone CIS processors (left panels) and for two processors of the invention (right panels) for signal levels of −36 (bottom) and −18 dB (top), for a fixed SNR of 0 dB, and for the condition when the signal is to the left and the noise to the right of the listener. Horizontal dotted lines depict the output amplitude for channel #5 of the standard CIS processor as a reference. The vertical arrows indicate the inter-aural (inter-processor) output amplitude for channel #5 but they are displaced to avoid clutter.

FIGS. 12a-12f. Show respective graphs of a comparison of peak excitation patterns (at time ~37 ms) for two stand-alone, standard CIS processors (left panels) and for two processors of the invention (right panels) for a fixed signal level of −12 dB and three different SNRs: −6 dB (top), 0 dB (middle), +6 dB (bottom). All are for a condition where the signal is to the left and noise to the right of the listener.

FIG. 16a. HRTF-filtered waveform for the word 'diga' on the left-ear. FIG. 16b. HRTF-filtered waveform for the word 'sastre' on the right-ear. FIG. 16c. Output amplitudes for the two standard CIS processors. FIG. 16d. Output amplitudes for the processor of the invention. Each panel illustrates the channel outputs for the right-ear (top lines) and the left-ear (bottom lines) processors. Note that the channel outputs for the two processors are sometimes identical and hence overlap.

PREFERRED EMBODIMENT OF THE INVENTION

In a preferred embodiment of the invention a user wears two cochlear implants, one in each ear, with corresponding sound processors capable of exchanging time-varying control signals and updating their frequency-specific compression maps adaptively in time. The exchange of control signals could be direct (i.e., from processor to processor) or indirect (from each processor to a remote control unit, to the contralateral processor); in any case the communication between the components of the cochlear implants could be wired or wireless. The rate of update of the control signals could be as fast as the operating sampling rate of the processors or as slow as twice the highest frequency in the channel envelopes (i.e., twice the cut-off frequency of the filter employed for envelope detection in each channel).

In some embodiments of the invention one cochlear implant may be used, being the cochlear implant responsible for capturing and processing any acoustic signal and simulating all the tasks that would otherwise be assigned to the other cochlear implant. A single-sided cochlear-implant user who wears a full system (implant+sound processor) in one ear and a processor-only (no implant) in the other ear may be envisaged too. Alternatively, a single-sided cochlear implant user whose single sound processor operates as if it was a bilateral with two different acoustic inputs, one from each ear (i.e., this would require a full cochlear implant in one ear plus a microphone in the non-implant ear). In these cases, it would still be possible to implement bilateral CIS processing and the pattern of electrical stimulation provided via the only available implant would preserve some of the argued benefits of bilateral processing.

Figure 1:
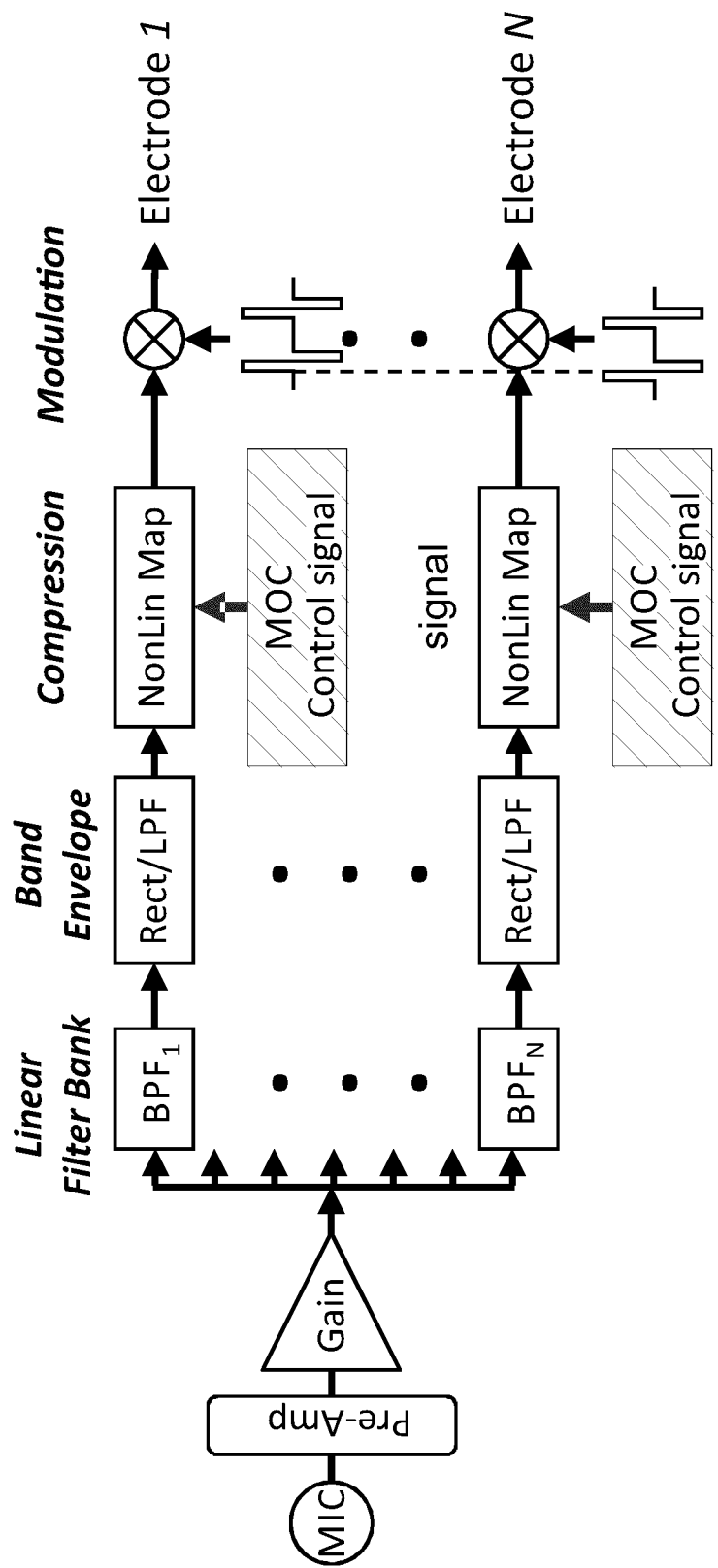
FIG. 1. Shows a diagram depicting an embodiment incorporating MOCR efferent control to a pulsatile CIS sound processor.

FIG. 1 partially illustrates a generic, state-of-the-art multichannel pulsatile CI sound processor. In this generic processor, sound is picked up by a microphone, processed by a pre-emphasis filter to enhance certain frequency components, typically high frequencies, and adjusted in overall level by an automatic gain control (AGC). The AGC and pre-emphasis filter may be swapped or implemented jointly. The resulting signal is then filtered through a bank of N linear bandpass filters (BPF). The envelope of the output signal from each band is then extracted. In the example shown in FIG. 1, the envelope is extracted by half-wave rectification (Rect.) followed by lowpass filtering (LPF), but different sound processors may use different envelope extraction algorithms. Finally, the envelope of each channel is compressed (NonLin Map) to map a wide range of acoustic pressure levels into a narrower dynamic range of tolerable electrical currents, typically from absolute threshold to most comfortable level. Lastly, the mapped enveloped is used to modulate trains of continuous interleaved electrical pulses that are delivered via corresponding electrodes.

Current clinical sound processing strategies, including the popular continuous interleaved sampling (CIS) strategy or the advanced combination encoders (ACE) are variations of this generic multichannel pulsatile processor. Other specific sound processing strategies may differ from this generic implementation in the number of channels, the relation between the number of filters and the number of activated electrodes, the details of how each channel's envelope is extracted, and how much temporal information is preserved.

With a pulsatile CI sound processor like that of FIG. 1, auditory sensitivity and dynamic range are determined independently for each electrode by the back-end amplitude compressors on nonlinear maps. Once customized, these nonlinear maps remain fixed and identical throughout acoustic stimuli and listening conditions. In natural acoustic hearing, by contrast, activation of medial olivocochear (MOC) efferents inhibits the cochlear gain and so cochlear sensitivity to low- and moderate-level sounds but not to high-level sounds. In other words, activation of MOC efferents 'linearizes' the cochlear response, hence reducing the cochlear dynamic range, and concomitantly cochlear tuning. These MOC effects on cochlear responses probably reduce auditory sensitivity, auditory dynamic range and auditory frequency selectivity. Insofar as the MOC may be activated in a reflexive manner by ipsi- and contralateral sounds, it is possible that in natural hearing cochlear gain (and tuning) may not be fixed but rather changing dynamically depending upon the characteristics of ipsi- and contralateral sounds. We propose that the fundamental effects of MOC activation may be mimicked in a CI by using adaptive (i.e., time varying) rather than fixed amplitude compressors or nonlinear maps. In other words, by allowing the nonlinear maps to vary dynamically in time (i.e., to be more or less compressive) depending upon appropriate control signals.

An important issue is what type of control signals should be used and how such control should be exerted. To our knowledge, there is no precedent research on this topic and so, in principle, any reasonable form of control might be useful and should be explored. However, some inspiration may be gained from the natural MOC.

Figure 2:
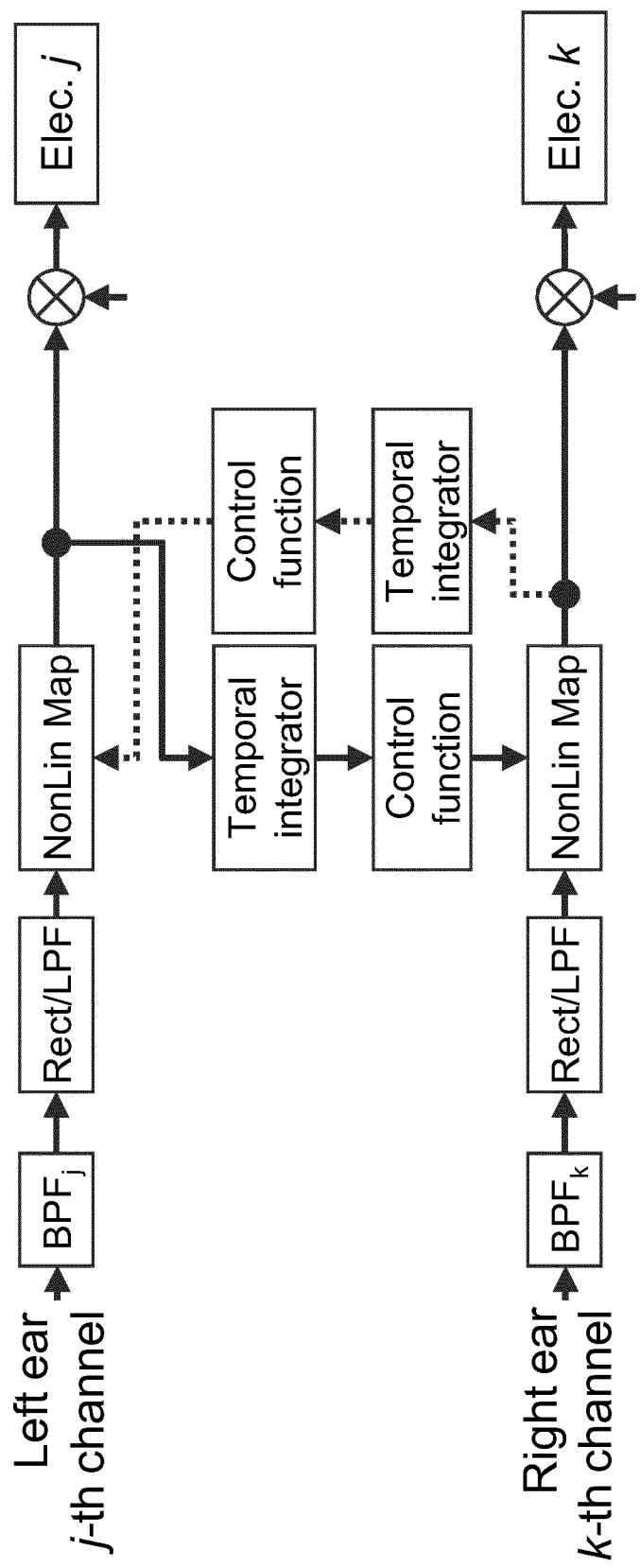
FIG. 2. Shows a diagram depicting an embodiment of a bilateral CIS processor with dynamic contralateral control. The top and bottom processing line represent only one generic frequency channel of the left-ear and right-ear CIS processors. The output signal from the nonlinear map of channel j in the left-ear processor is time-weighted and integrated in time and the result is used to set the nonlinear map of channel k in the right-ear processor.

Let us first consider how to mimic contralateral MOC reflex (MOCR) control with a binaural CIS processor. In natural hearing, the amount of cochlear gain reduction increases with increasing the level of the contralateral MOCR elicitor sound. In fact, it may be reasonably assumed that cochlear gain reduction is proportional to the response of the auditory nerve directly stimulated by MOCR elicitor sound rather than to the overall level of the elicitor itself. Furthermore, MOC inhibition is greater when the frequency of contralateral MOCR elicitor is between half-an-octave to one-octave below the characteristic frequency of the inhibited cochlear region. It is also greater when the contralateral elicitor is broadband than when it is narrowband. Lastly, MOC inhibition takes some time to build up or decay after the contralateral MOR elicitor is switched on and off, respectively. The present invention proposes to mimic contralateral MOCR efferent control by using a bilateral CIS processor where the amount of compression on a given frequency channel of one processor varies dynamically depending upon the time-weighted output energy from an appropriate frequency channel (or channels) in the contralateral processor, as shown in FIG. 2 where the control is mutual between the two frequency channels but this does not need to be the case. That is, in the most general case, channel numbers may be different for the two processors; or even more, channel j in the left-ear processor could control channel k in the right-ear processor, and the latter could control channel i in the left processor.

For example, the compression on the k-th channel of the right processor could depend upon the time-weighted output energy from the j-th frequency channel in the left processor (or upon the combined energy from a number of channels in the left processor). Inspired by the natural MOC, the greater the contralateral output energy, the more linear the compressor and the lower the gain to low level sounds should be. Furthermore, insofar as the output energy can vary in time following the acoustic stimulus, the control should be dynamic (i.e., time varying). The controlled and controlling channels in the two processors, j and k, could have the same or different frequencies (e.g., to closer mimic contralateral MOC control, the contralateral controlling channel should be lower in frequency than the controlled channel). Most importantly, the contralateral control should be mutual. That is, the left processor should control the right processor and vice versa, although this does not mean that the controlled and controlling channels should be paired in frequency. A particular example implementation of this kind of control is developed and tested below.

So far, we have considered an MOCR-inspired contralateral control of the CIS back-end compressors. Just like efferent MOC cochlear inhibition may be activated by ipsilateral and contralateral sounds, an alternative or additional form of control could be exerted ipsilaterally. In natural hearing, ipsilateral MOCR efferent effects share many of the characteristics of the contralateral MOCR control, except, perhaps, that ipsilateral MOC inhibition is greatest when MOC elicitors are of the same frequency as the test tone. Therefore, ipsilateral control of back-end CIS compressors could be implemented using the approach described above (FIG. 2) for contralateral control except that the controlled and the controlling channels should be the same (i.e., each channel in a given processor would be controlled by itself) or, in the most generic case, would be from the same ear. Natural ipsilateral and contralateral MOCR efferent effects appear additive Therefore, theoretically ipsilateral and contralateral control of back-end compressors in a CIS processor should occur simultaneously.

The range of possibilities is enormous and the actual implementation of contralateral and/or ipsilateral MOCR control could be difficult, and the potential benefits uncertain. In the next sections, we describe a particular example implementation of contralateral MOCR control in a bilateral CIS processor and its potential benefits.

Figures 3A, 3B:
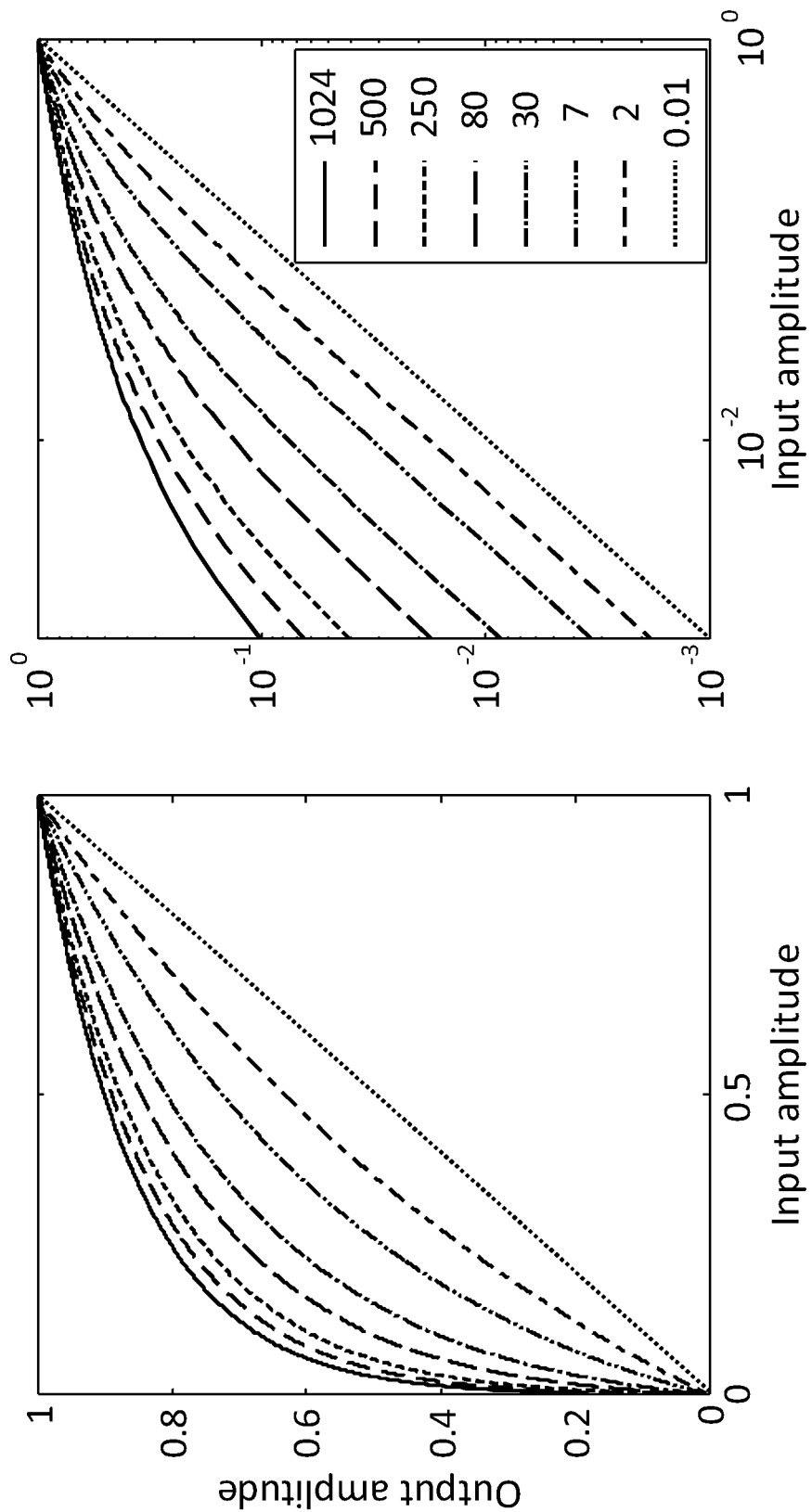
FIGS. 3a, 3b. Show graphs of a compression function known as IBK for different values of parameter c, as indicated by the inset. The two panels depict identical data and differ in that the input and output amplitudes are in linear and logarithmic scales in the left and right panels, respectively. Note that the compression function is approximately linear for c=0.01 (dotted line) and that typically c=500.
Figure 4A:
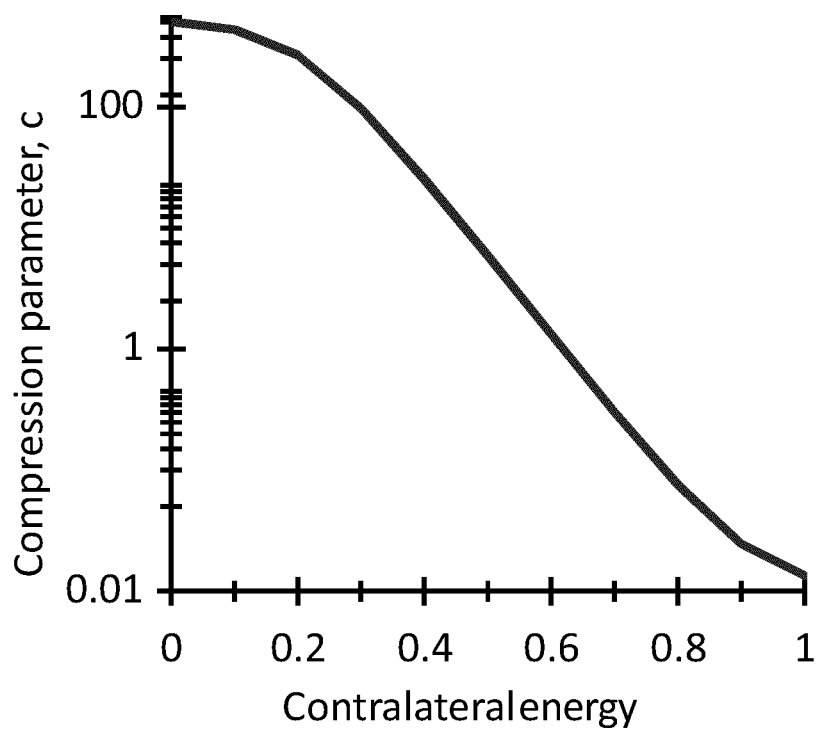
FIGS. 4a-4c. Show graphs depicting the relationship between the compression parameter, c, the contralateral output energy, E, and the input and output amplitudes for a sigmoidal control function with $c_b$=525, $c_a$=0.01, α=15, and β=0.2.
Figure 4B:
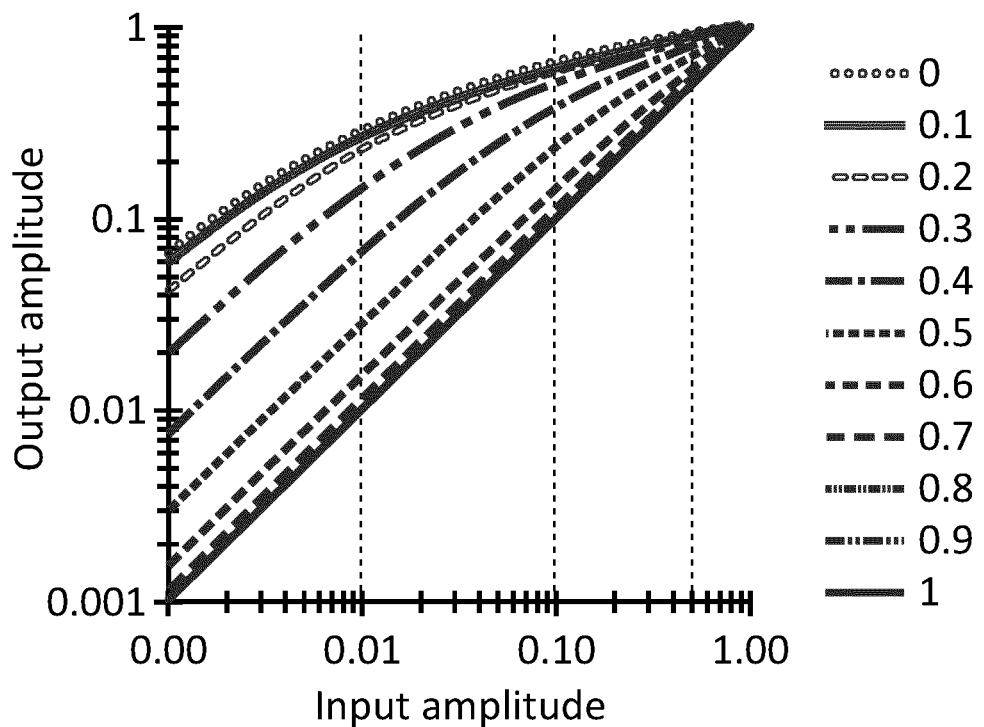
Figure 4C:
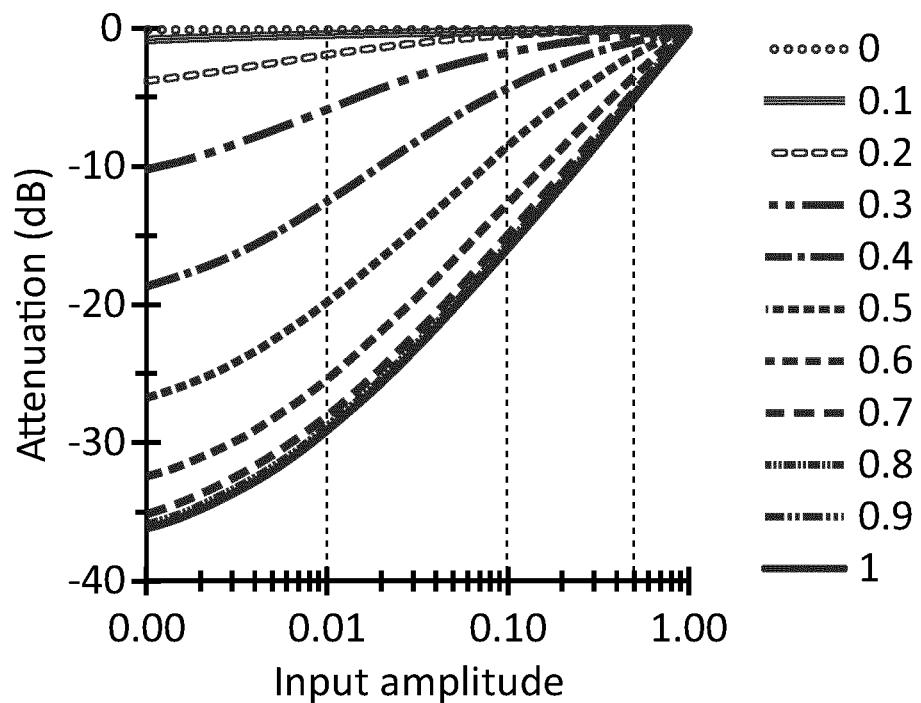
Figure 4D:
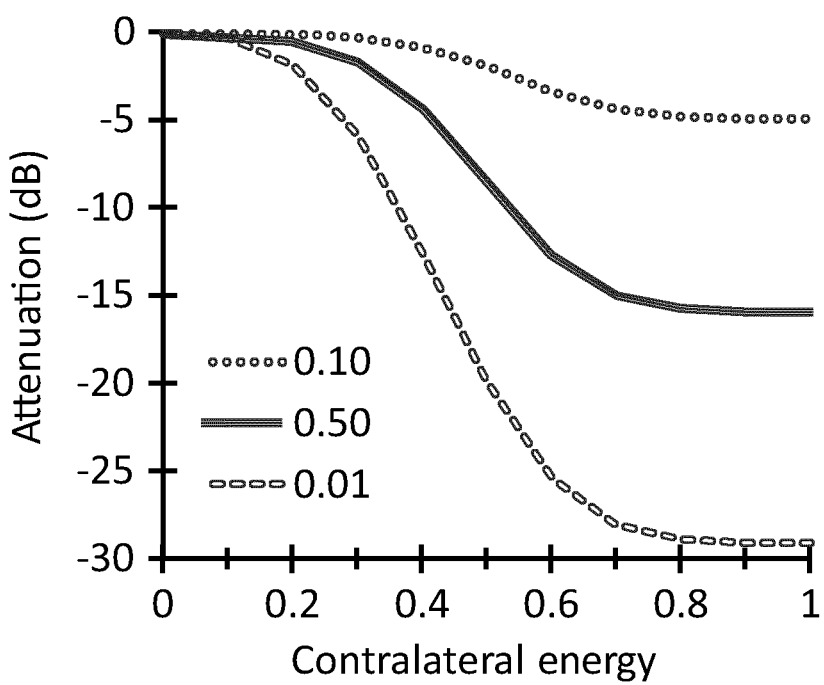
FIG. 4D illustrates the amount of inhibition as a function of contralateral energy for three fixed input amplitudes of 0.01, 0.1 and 0.5.

A compression function typically used by CIS processors, known as IBK mapping function (or map law), is given by the following equation:

$$y = \frac{\log(1 + c \cdot x)}{\log(1 + c)}, \quad \text{(Eq. 1)}$$

where x and y are the input and output amplitudes to/from the compressor, respectively, both of them assumed to be within the interval [0,1[; and c is a parameter that the determines the amount of compression. FIG. 3 shows that the smaller the value of c the more linear the function is. A typical value is c=500. For monaural CI users, c may be identical or different across frequency channels but is otherwise fixed (i.e., time-invariant and independent of the stimulus). For bilateral CI users, different values of c may be used for the left-ear and right-ear processors and these values are determined independently during the fitting of each device. Let us refer to the corresponding value for a given channel of either processor as $c_{std}$.

Consider now a bilateral CI user. Inspired by the characteristics of contralateral MOCR control, we propose a bilateral CIS sound processor where c varies adaptively in time depending upon the time-weighted output energy from the corresponding contralateral channel. For convenience, in this example implementation we are disregarding the half-octave frequency shift of the contralateral MOCR efferent described elsewhere, hence in the proposed bilateral processor the contralateral control is for matching frequency channels.

An instantaneous value of c(t) for any given frequency channel in the left-ear processor $c_L(t)$ is inversely related with the output energy from the corresponding channel in the right-ear (contralateral) processor, $E_R(t)$, and vice versa. For reasons which are explained below, in this example implementation we have assumed a sigmoidal relationship of the form:

$$c_L = \frac{c_a - c_b}{1 + e^{-\alpha[E_R(t) - \beta]}} + c_b, \quad \text{(Eq. 2.a)}$$

$$c_R = \frac{c_a - c_b}{1 + e^{-\alpha[E_L(t) - \beta]}} + c_b, \quad \text{(Eq. 2.b)}$$

where $E_R(t)$ and $E_L(t)$ are assumed to be between 0 and 1 (see below), and $c_a$ and $c_b$ determine the compression range over which the map law can vary, with $c_b$ and $c_a$ corresponding to the most and the least compressive values, respectively. In principle, $c_b$ should be equal or close to the standard value in a monaural CIS system (i.e., $c_b = c_{std}$) to warrant that in the absence of any contralateral control, the ipsilateral processor behaves as a standard one [i.e., $c_L = c_{std}$ for $E_R(t) = 0$]. In the extreme, $c_a$ could correspond to a linear system, so that with maximum contralateral output and the map law becomes fully linear [i.e., $c_L = c_a$ for $E_R(t) = 1$]. In other words, the map law is bounded within linearity and a standard CIS. Both in Eq.2.a and Eq.2.b, α is a parameter that determines the rate of change of c with E(t), and β is the value of E(t) for which $c = (c_a + c_b)/2$. Note that in Eq.2.a and Eq. 2.b), α, β, $c_a$ and $c_b$ are assumed to be identical for both processors, right-ear and left-ear processors, but this needs not be the case.

FIG. 4 illustrates the relationship between the compression parameter, c, the contralateral energy, E, the input amplitude and output amplitude for a sigmoidal relationship with $c_b = 525$ and $c_a = 0.01$, α=15, and β=0.2. FIG. 4A illustrates the actual control function (Eq. 2.a or Eq. 2.b). Note that c~500, the default standard value, for E=0 and that it decreases with increasing E until it equals 0.01 (a linear map law) for E=1. FIG. 4B shows compression functions for ten different values of the contralateral energy linearly distributed between 0 and 1. Note that the function becomes gradually more linear (i.e., the output to low-level input is attenuated gradually more) with increasing contralateral energy. FIG. 4C illustrates the amount of inhibition (in dB re maximum output) as a function of input amplitude. Note that the largest inhibition is about 35 dB and occurs for a contralateral energy of 1 and input amplitude of 0.001. Lastly, FIG. 4D illustrates the amount of inhibition as a function of contralateral energy for three fixed input amplitudes of 0.01, 0.1 and 0.5. This figure shows that the rate of change inhibition with a change in E (i.e., the slope of the function) is greatest for E~0.5 regardless of the input amplitude. This is not coincidental. Indeed, α and β were manually optimized with this criterion in mind on the assumption that the AGC of a CI sound processor is specifically designed for accommodating stimulus amplitudes around 0.5. Of course, different parameters and/or a different control function could be employed if the criterion was different.

The instantaneous output energy from the contralateral processor, E(t), was calculated as the time-weighted root-mean-square (RMS) amplitude over a preceding time period, T, as follows:

$$E(t) = \left[ \frac{1}{T} \int_{t-T}^{t} y^2(t-\tau) h(\tau) d\tau \right]^{0.5} \quad \text{(Eq. 3)}$$

where y(t) is the waveform at the output of the compressor, T is the integration period, and h(τ) is an exponentially decaying time-window of the form:

$$h(\tau) = w \cdot \exp\left(-\frac{\tau}{\tau_a}\right) + (1-w) \cdot \exp\left(-\frac{\tau}{\tau_b}\right). \quad \text{(Eq. 4)}$$

In Eq. (4), $\tau_a$ and $\tau_b$ are fast and a slow decay constants, respectively, and w is a parameter valued within the range [0, 1], that determines the amplitude when the slow time constant takes over the fast one. Note that the maximum amplitude of the time window equals 1 at time zero (τ=0). Note also that E(t) is valued between 0 and 1 because both y(t) and h(t) are always valued between 0 and 1 and the integral (Eq. 3) is normalized to the integration period, T.

Figure 5:
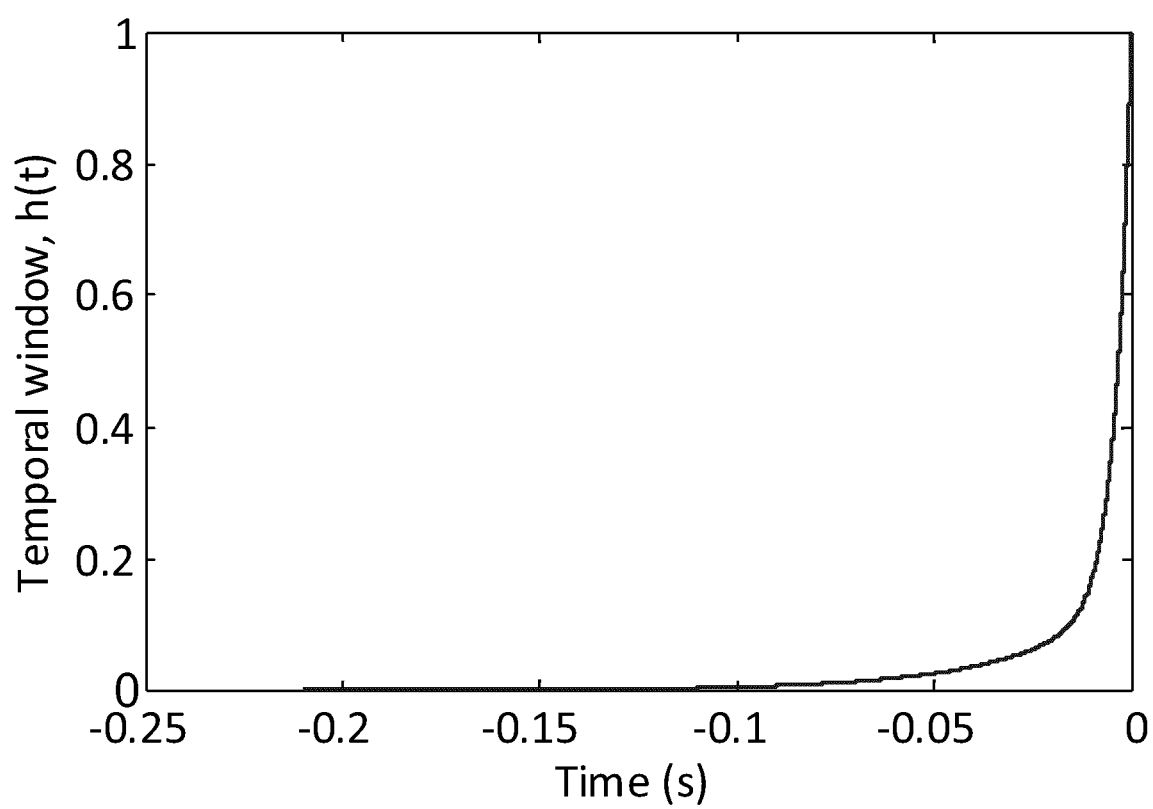
FIG. 5. Shows a graph depicting a temporal window, h(t), for $τ_a$=4 ms, $τ_b$=29 ms, and w=0.86.

It is important to note that for each time instant t, E(t), is the time-weighted RMS energy of the channel output waveform, y(t), in the preceding time period t−T, and that the time window gives more weight to the energy in immediate than in the remote past, depending on the time constants $\tau_a$ and $\tau_b$. FIG. 5 illustrates the shape of an example time window.

Another aspect of the invention is a processor operative to implement the method of the invention. The processor is a MOCR-inspired bilateral processor (MOC-CIS) with contralaterally controlled adaptive compression and it was then compared with a standard bilateral CIS processor (STD-CIS) with fixed compression. The latter consisted of two identical and functionally independent CIS processors, one for each ear. The MOC-CIS processor consisted of two CIS processors that were identical to the STD-CIS except that their compression functions in each channel of either processor were adaptively controlled by the contralateral processor, as described above in the method of the invention. Comparisons were based on analyses of the channel outputs after compression (i.e., the output from the NonLin Map. in FIG. 1).

In this comparison, the processor of the invention comprises no front-end gain or AGC and the pre-emphasis filter was a Butterworth $1^{st}$-order high-pass filter with a cut-off frequency of 1200 Hz. The linear filter bank consisted of 12, $6^{th}$-order Butterworth bandpass filters. The cut-off frequencies of the filters were approximately logarithmically spaced throughout a frequency range from 300 Hz to 8.5 kHz (the actual cutoff frequencies were obtained using an undisclosed function property of MED-EL®). Adjacent filters overlapped at their cut-off frequencies. The envelope of the output signal from each filter was extracted by full-wave rectification (FWR) and low-pass filtering through a $4^{th}$-order Butterworth filter with a cut-off frequency of 200 Hz. Envelope amplitudes spanned the range [0,1[ and were compressed using IBK mapping (Eq. 1). For the STD-CIS binaural processor, both the right-ear and left-ear processors were identical and were set with a compression value of $c=c_{std}=500$, a typical value used in MED-EL® clinical devices.

The adaptive MOC-CIS processor was implemented using the sigmoidal contralateral control function described above (Eq. 2) with the parameters used to produce FIG. 4 ($c_a=0.01$, $c_b=525$, α=15, β=0.2). The time-weighted output energy from the contralateral channel, E(t) (Eq. 3), was calculated using a time window (Eq. 4) with the following parameters: w=0.86, $\tau_a=4$, $\tau_b=29$ ms. These parameters were arbitrarily chosen. The integration time period (T, Eq. 3) was set equal to the period required for the window amplitude to decay from its maximum value of 1 to an arbitrary value of 0.01. For the chosen parameters, T became equal to 76 ms. A longer T would increase the computational time without a significant change in the results. Unless otherwise stated, the compression parameter, c, was calculated anew on a sample-by-sample basis, depending on E(t).

It is important to stress that the bilateral STD-CIS and MOC-CIS differed only in their compression functions. For the STD-CIS, compression was fixed and identical to a typical clinical value (c=500). For the MOC-CIS, compression was adaptively changed as explained above with the STD-CIS being an upper boundary for MOC-CIS compression.

All processors were implemented digitally in the time domain, in Matlab™ and evaluated using a sampling frequency of 44.1 kHz.

Performance for the STD-CIS and MOC-CIS processors was compared for different signals in different types and amounts of noise. Signals were available as digital recordings or were generated digitally in the time domain. Stimulus levels are expressed as RMS amplitudes in dB re the RMS amplitude a 1-kHz sinusoid with peak amplitude of 1 (i.e., dB re √2). To avoid transient onset filtering effects, signals were sometimes preceded and/or followed by a silence segment, and/or were gated with raised-square onset/offset ramps. Silence segments and ramps were included in RMS level calculations.

Contralateral control effects in the MOC-CIS processor were expected to be different depending upon the relative stimulus levels and frequency spectra at each ear. For this reason, and to assess performance in binaural, spatially realistic scenarios, all stimuli were filtered through KEMAR head-related transfer functions (HRTFs) prior to their processing through the MOC-CIS or STD-CIS. HRTFs were applied as 512-point finite impulse response (FIR) filters. STD-CIS and MOC-CIS performance was compared assuming sound sources at eye level (0° of elevation) and for three different horizontal locations of the signal and noise (or interferer): signal and noise in front of the listener ($S_F N_F$); signal on the left with noise in front of the listener ($S_L N_F$); and signal on the left with noise on the right of the listener ($S_L N_R$).

The basic properties of the MOC-CIS are illustrated in the following sections by analyzing its channel output signals in response to a binaural, 1-kHz pure tone signal of 50 ms of duration with 10-ms cosine squared onset and offset ramps. In all cases, the pure tone signal is preceded and followed by 10 ms of silence. Unless otherwise stated, signal level was −6 dB.

FIG. 6 shows a comparison of STD-CIS and MOC-CIS channel outputs for a 1-kHz pure tone signal in quiet, and for three different signal locations: left ($S_L$), front ($S_F$), and right ($S_R$). Blue and red lines depict channel output signals for the left- and right-ear processor, respectively. Note the overlap between the red and blue lines in some conditions. Output amplitude is greatest for channel #5 (with channel numbering starting from the bottom of each panel) because the signal frequency (1 kHz) falls within the pass band of that filter. Given that the stimulus was binaural and filtered through appropriate HRTFs, there is an acoustic inter-aural level difference (ILD). For this reason, the amplitude of channel #5 is greater for the right-ear than for the left-ear processor when the signal is on the right (FIG. 6C) and the other way round when the signal is on the left (FIG. 6A). When the signal is in front, the output amplitudes are identical for the left- and right-ear processors, hence the overlap between the blue and red curves in FIG. 6B. This behavior is reasonable and is qualitatively comparable for the STD-CIS and for the MOC-CIS processors (compare the top and bottom panels in FIG. 6).

Strikingly, however, the inter-aural output amplitude difference (IOD) for channel #5 is greater for the MOC-CIS than for the STD-CIS processor. This result is more clearly shown in FIG. 7, which depicts peak output amplitude at time ~37 ms as a function of channel number for the right-ear and left-ear processors. Note that these results are for a stimulus located on the right only ($S_R$). Clearly, the IOD for the MOC-CIS processor ($IOD_{MOC-CIS}$ in FIG. 7B) is greater than the IOD for the STD-CIS processor ($IOD_{STD-CIS}$ in FIG. 7A). This is because in the MOC-CIS processor, the gain of channel #5 in the two MOC-CIS processors is inhibited in direct proportion to the output amplitude from the corresponding channel in the contralateral processor. Given that the acoustic stimulus is binaural and that in the particular example shown in FIG. 7 its level is greater on the right ear, the output amplitude is also greater for the right than for the left processor. Hence, the right-ear processor inhibits the left-ear processor more than the other way around.

Figures 7A, 7B:
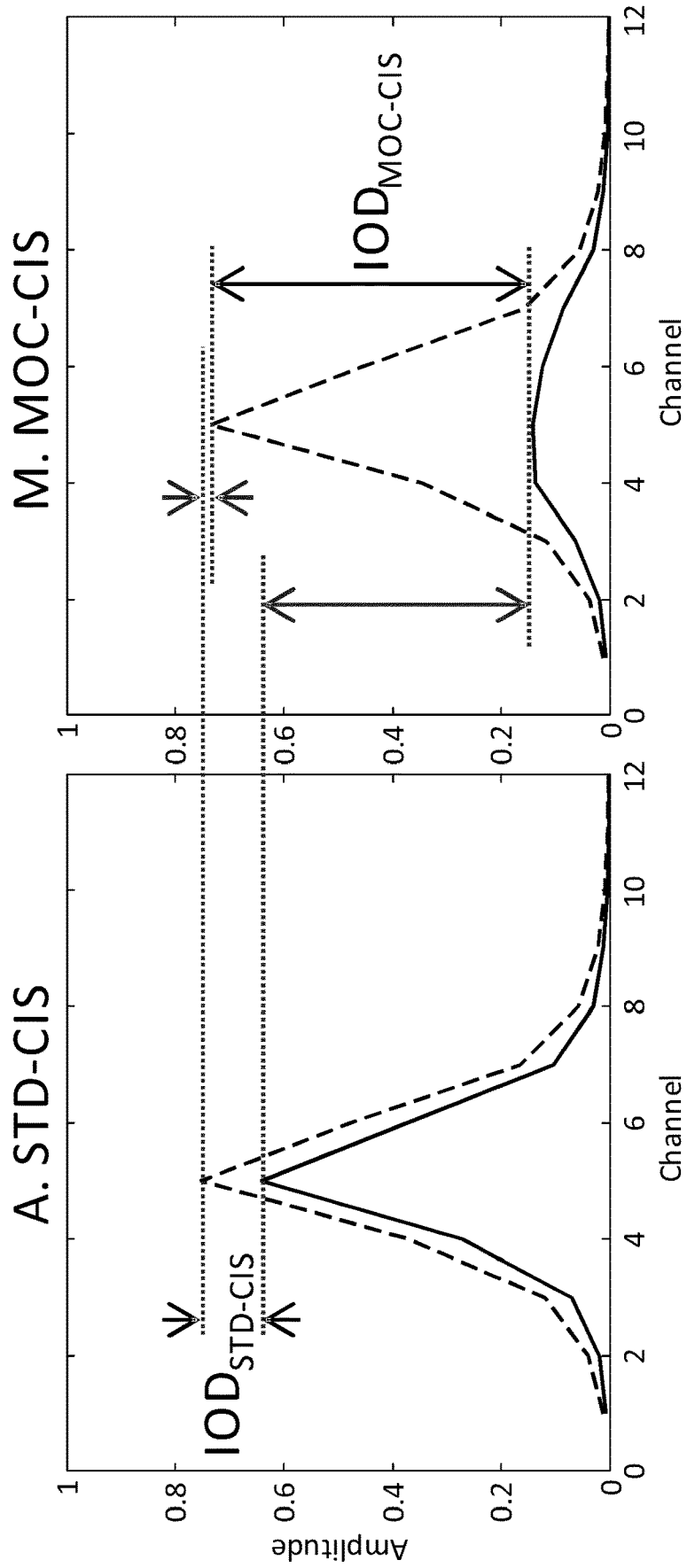
FIGS. 7a,7b. Show respective graphs of a comparison of the left-ear (lower line) and right-ear (upper lines) output peak excitation patterns for the two stand-alone CIS processors (FIG. 7a) and for two processors of the invention (FIG. 7b) at time ~37 ms for a 1-kHz pure tone signal located on the right.

Of course, the right-ear processor is also inhibited by the left-ear processor to some extent. This is shown in FIG. 7 by the fact that the peak amplitude of channel #5 in the right-ear processor is slightly lower for the MOC-CIS than for the STD-CIS processor. In the absence of contralateral inhibition, the MOC-CIS is identical to the STD-CIS. Hence, the slightly smaller output of the right-ear MOC-CIS processor compared to the STD-CIS processor (red arrows in FIG. 7B) is indicative of some inhibition. The amount of this inhibition is, however, much smaller than for the left processor (blue arrows in FIG. 7B) for two reasons: (1) because the stimulus level is lower on the left ear; and (2) because the gain in the left processor is further inhibited by the stronger right-ear processor output. In other words, the amount of contralateral inhibition is asymmetrical because it depends on the processors' output amplitudes rather on their input amplitudes.

Figure 8A:
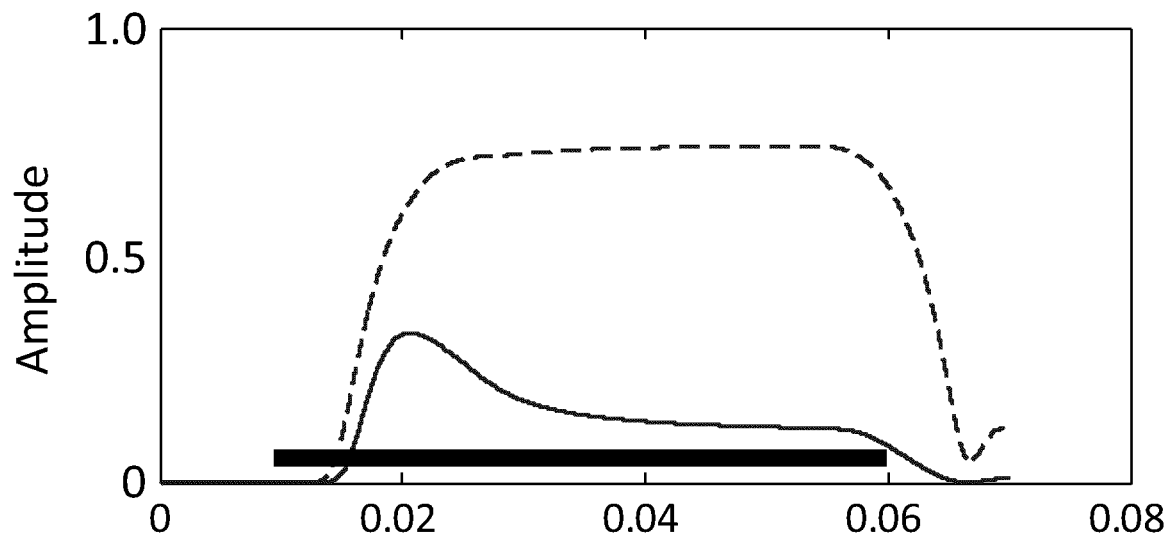
FIGS. 8a, 8b. Show respective graphs of the time course of the contralateral effect for channel #5 of the bilateral CIS processor of the invention, and for a condition where the signal is in quiet and on the right.
Figure 8B:
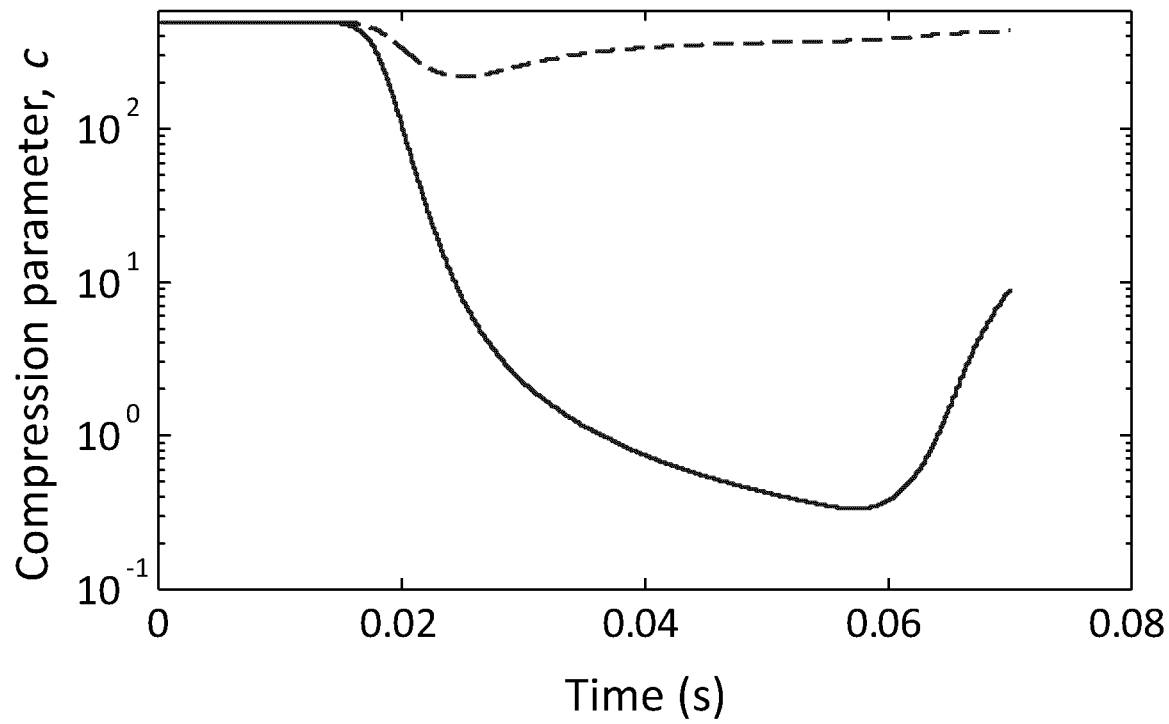

Since stimulus was sustained in time and the amount of compression was re-calculated on a sample-by-sample basis, the IOD for channel #5 is relatively smaller at the stimulus onset and increases gradually in time until it reaches a plateau effect. The time course of this effect is illustrated in FIG. 8. Note that at time=0, compression is identical (c~500) for the right-ear and left-ear processors. Then, as the output amplitude from the right-ear processor increases, compression on the left-ear processor decreases (i.e., the map law becomes more linear). This decreases the output amplitude from the left-ear processor even further, which in turn reduces its inhibitory effect on the right-ear processor.

Unlike the MOC-CIS, whose output amplitudes vary depending on the contralateral control, compression in the two STD-CIS processors is fixed. Hence, the smaller $IOD_{STD-CIS}$ (relative to $IOD_{MOC-CIS}$) (FIG. 7A) reflects only the acoustic, HRTF-related, ILD. In summary, MOC-CIS presumably conveys a better lateralized signal compared to the STD-CIS.

Figures 10D, 10E, 10F:
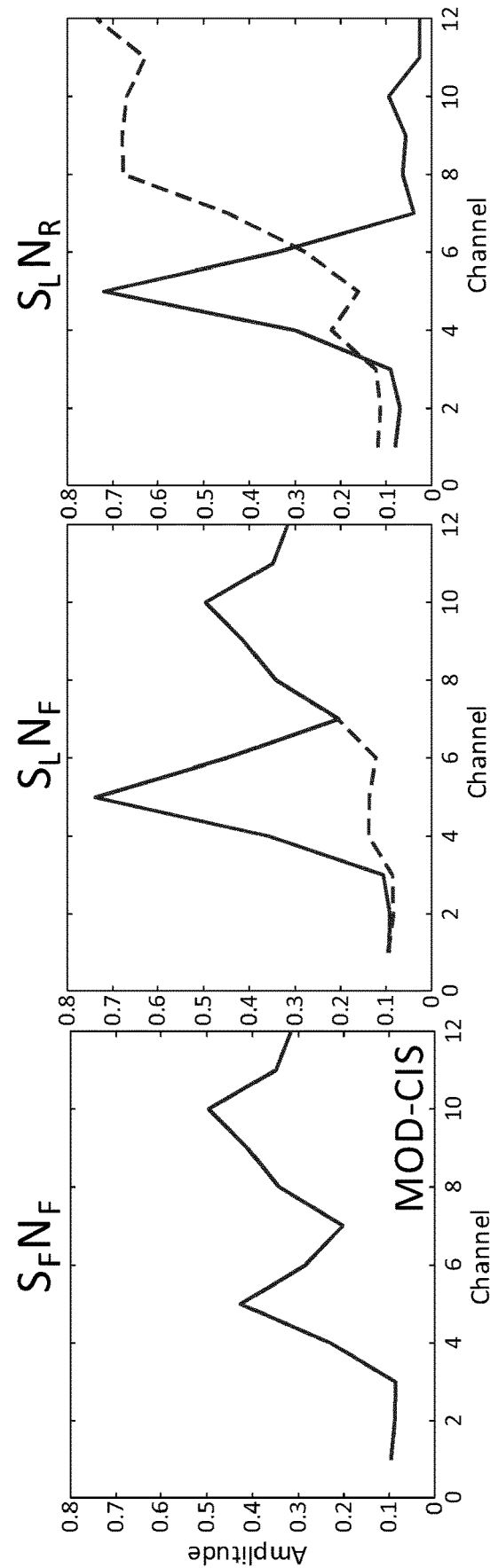

FIG. 9 illustrates channel outputs for the STD-CIS and the MOC-CIS processors for a −6 dB, 1-kHz pure tone signal in 0 dB SNR white noise. FIG. 10 illustrates corresponding peak excitation patterns for time ~37 ms. An identical noise token (i.e., frozen noise) was used to produce all these figures to facilitate the comparison across processors and conditions. Let us first consider the $S_F N_F$ condition (left panels in FIG. 9 and FIG. 10). In this condition, channel outputs are identical for the left-ear and right-ear processors. Peak output amplitude, however, is greater for the STD-CIS than for the MOC-CIS (i.e., compare FIG. 10A with FIG. 10D). This is because the stimulus is identical at the two ears, hence the two MOC-CIS processors inhibit each other by the same amount, linearizing the map law and reducing the output amplitude compared to the STD-CIS. Although this linearization might reduce audibility, it could have other potential benefits. For example, it enhances amplitude modulation. Indeed, modulation in channels #8 to #10 is deeper for the MOC-CIS (FIG. 9D) than for the STD-CIS (FIG. 9D). This issue is discussed further below.

Let us now consider the $S_L N_F$ condition (middle panels in FIG. 9 and FIG. 10). In this condition, identical noise levels reach the two ears but signal level is higher on the left than on the right ear. For the STD-CIS processor, this causes a relatively small IOD in the channels with frequencies around the signal frequency (channels #4 to #6, FIG. 10B) and a relatively high output for channels most sensitive to the noise (channels #8 to #12). Results are strikingly different for the MOC-CIS processor (FIG. 10E). Because the noise level is identical for the two ears, it inhibits itself contralaterally, hence reduces the response of those channels most responsive to the noise (#8 to #12), as described previously for the $S_F N_F$ condition. The level of the pure tone signal, however, is higher on the left ear than on the right ear. Therefore, the larger signal output in the left-ear processor inhibits the right-ear processor more than the other way round. As shown in FIG. 10E, the net effect is a very large IOD for the signal channels (#4 to #6) accompanied by reduced excitation to the noise (channels #8 to #12). In perceptual terms, presumably, the MOC-CIS would convey a less noisy and better lateralized signal.

Lastly, let us consider the $S_L N_R$. In this case, the noise level is higher on the right than on the left ear and signal level is higher on the left than on the right ear. In other words, the effective SNR is greater on the left than on the right ear. This explains the STD-CIS excitation patterns shown in FIG. 10C: the output from the signal most-sensitive channel (#5) is greater for the left than for the right ear, while the output from the noise most-sensitive channels (#8 to #12) is larger for the right than for the left ear. The excitation patterns for the MOC-CIS processor (FIG. 10F) are strikingly different. Because of contralateral inhibition, the left-ear processor responds to (i.e., conveys) the signal whilst the right-ear processor responds mostly to the noise. Furthermore, the IOD for the signal (channel #5) is much greater than for the STD-CIS. In perceptual terms, presumably, the effect would be a much less noisy and better lateralized signal and noise.

Figures 11C, 11D:
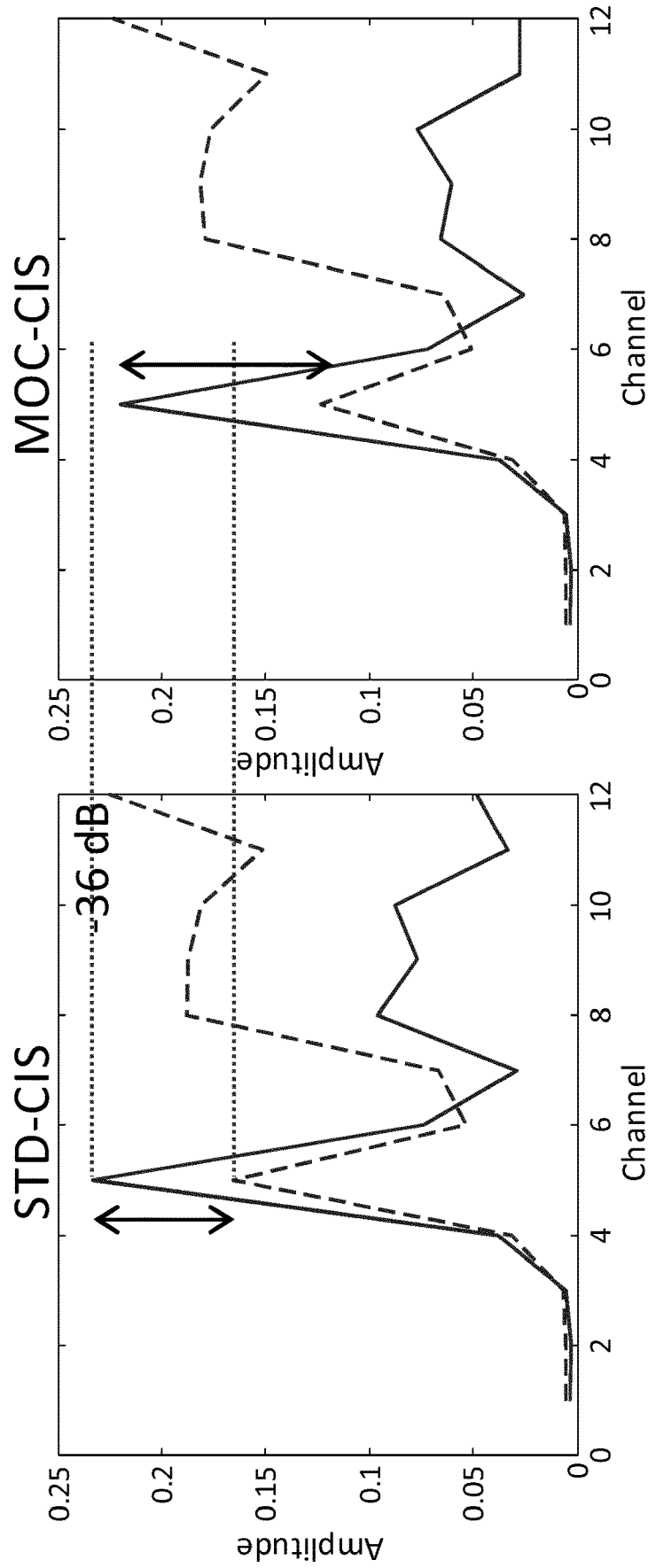
Figure 12D:
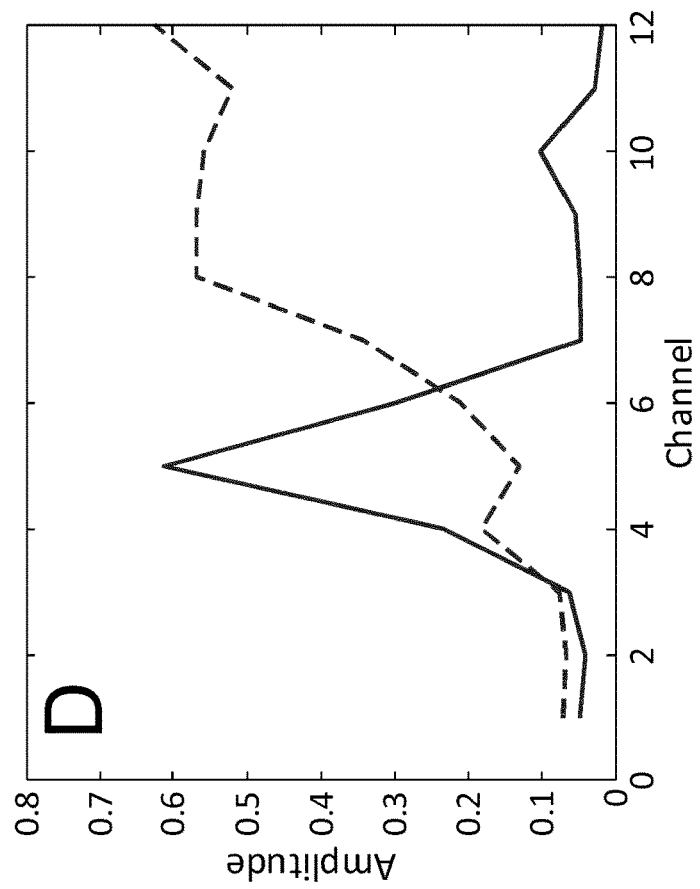
Figure 12C:
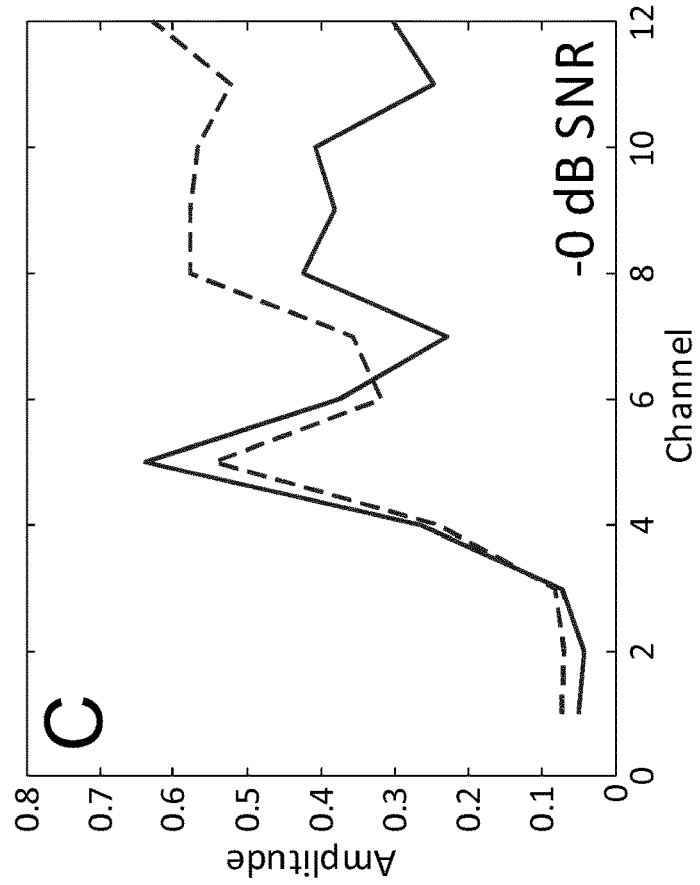
Figure 12F:
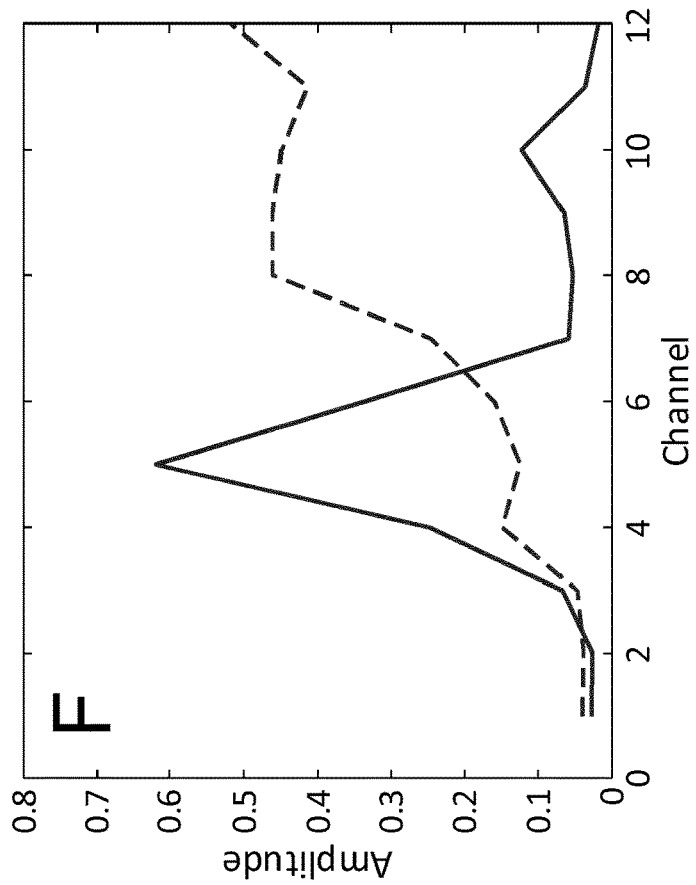
Figure 12E:
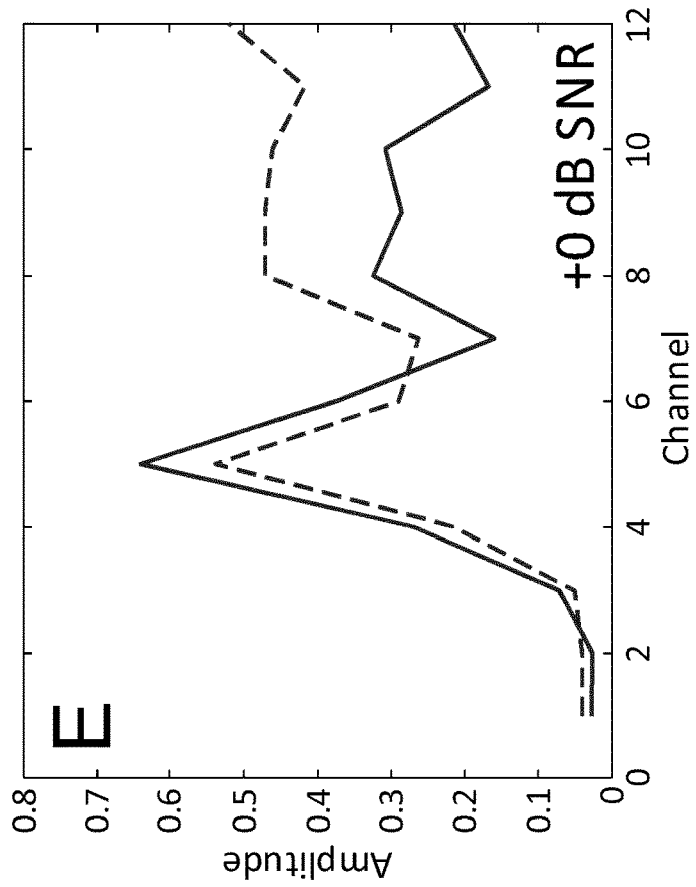

The effects described so far were for a signal level of −6 dB but they hold for a wide range of signal levels. As an example, FIG. 11 illustrates peak excitation patterns for the STD-CIS (left panels) and the MOC-CIS (right panels) for the $S_L N_R$ condition, and for signal levels of −36 (bottom) and −18 dB (top). All results are for 0 dB SNR. The horizontal dotted lines are for reference only and depict peak output amplitudes for channel #5 for the left-ear and right-ear STD-CIS processors. Note that the IOD for the signal most sensitive channel #5 (depicted by vertical arrows) is higher for MOC-CIS than for STD-CIS for the two levels, particularly for −18. Note also that the noise reduction on channels #8 to #12 of the left-ear MOC-CIS processor, which has been shown to occur for a signal level of −6 dB (FIG. 10F), continues to occur even for signal levels of −18 dB (compare FIGS. 11A and 11B), and to a lesser extent also for −36 dB (compare FIGS. 11O and 11D).

The benefits of the MOC-CIS described above also hold for a wide range of SNR, even for negative SNR. As an example, FIG. 12 shows peak excitation patterns (at time ~0.37 ms) for the STD-CIS (left panels) and the MOC-CIS (right panels) for the $S_LN_R$ condition, and for SNR of −6 dB (top), 0 dB (middle), and +6 dB (bottom). All results are for a fixed signal level of −12 dB. Note that for the signal most-sensitive channel #5, $IOD_{MOC-CIS}$ is higher than $IOC_{STD-CIS}$ for all three SNRs. Note also that the noise reduction on channels #8 to #12 of the left-ear MOC-CIS processor continues to occur even for −6 dB SNR (compare FIG. 12B with 12A).

Although the robustness of the benefits of the MOC-CIS across signal levels and SNR have been illustrated for a particular spatial condition ($S_FN_R$), the effects described thus far are equally robust for other locations.

Figure 13:
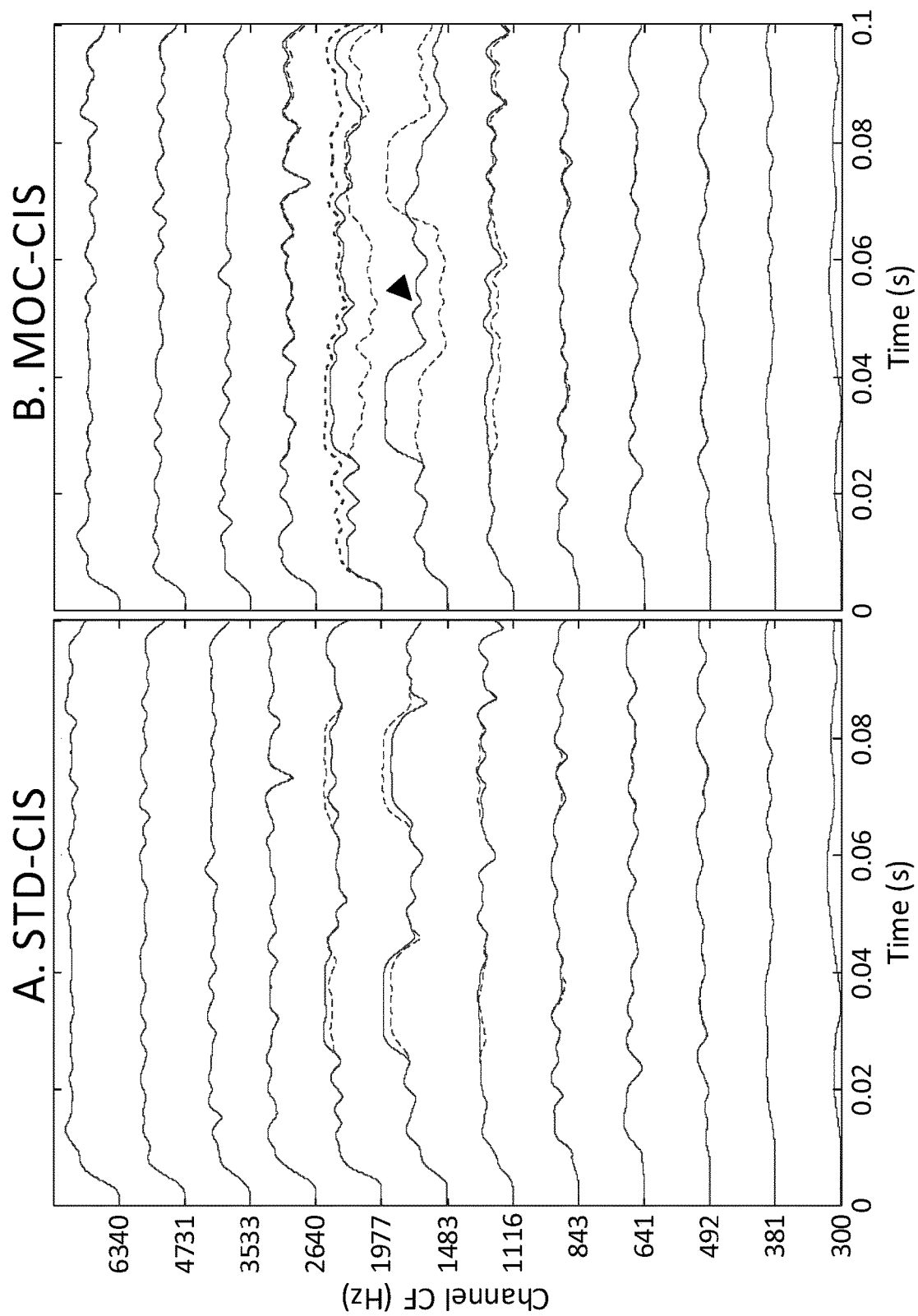
FIGS. 13a,13b. Show respective graphs of a comparison of channel outputs for two standard, stand-alone CIS processors (FIG. 13a) and the two processors of the invention (FIG. 13b) to two successive tone pips separated by a 20-ms time interval, and embedded in frozen noise. The first and second tone pips are presented to the left ear and right ear, respectively. Tone frequency is 1.9 kHz, tone level is −4.6 dB and the SNR is +3 dB. Blue and red curves illustrate channel outputs for the left- and right-ear processors, respectively.

The MOC-CIS processor of the invention involves a contralateral feedback and one might think this could make the MOC-CIS unstable. FIG. 13 allows assessing stability by comparison of channel outputs for the STD-CIS (A) and MOC-CIS (B) processors to a carefully chosen stimulus. The stimulus consists of 20-ms of silence followed by a 20-ms tone pip presented to the left ear, followed by 20-ms silence, followed by a 20-ms tone pip presented to the right ear, followed by 20 ms of silence. The two tone pips had identical frequency (1.9 kHz) and were presented in identical (frozen) noise to the two ears. The noise lasted for the entire stimulus duration (100 ms). The tone pips and the noise were gated with 5-ms and 10-ms cosine-squared onset and offset ramps, respectively.

FIG. 13A shows the output from the STD-CIS processor for reference. The two tone pips are conveyed mostly by channel #7. The output to the first tone pip is larger for the left ear than for the right ear because the first pip was presented to the left ear and the HRTF introduced an ILD; the output to the second tone pip is larger for the right-ear than for the left-ear processor because the second tone pip was presented to the right ear. Outputs are identical over silence intervals or over frequency channels remote from the tone-pip frequency because the noise was identical at the two ears.

FIG. 13B shows corresponding output amplitudes for the MOC-CIS processor. Note that, in this case, the left-ear and right-ear outputs do not always overlap in absence of the tone-pip signals. For example, for channel #8 the left-ear output gets higher than the right-ear output after the onset of the first tone pip but continues being higher even after the offset of the first tone pip. The same happens in channel #7 over the time interval between the two tone pips (arrow in FIG. 13B). This shows that the MOC-CIS system can be 'unstable' in the sense that a small inter-aural difference between the inputs or the outputs to/from the two compressors may be sufficient for an inter-aural output difference to gradually increase and propagate in time even after the stimulus causing such a difference ceases.

This type of instability is safe and may be physiologically plausible. It is safe because compression in the MOC-CIS is always less than or equal to STD-CIS compression. Hence, the output amplitude for the STD-CIS processor is an upper boundary to MOC-CIS output amplitude for any channel in any condition. To demonstrate this, the green line in FIG. 13B (channel #8) is a re-plot of the STD-CIS right-ear output. Note that despite the instability, the amplitude of the MOC-CIS processor never exceeds that of the STD-CIS.

The instability in question may also be physiologically plausible. In acoustic hearing in reverberant environments, a sound is perceived as originating from the location indicated by the first wave front, a phenomenon known as the precedence effect. FIG. 13B suggests that the left-ear dominates the binaural MOC-CIS response to the second top pip (at least for channels #6 and #8), and hence the two tone sequence might be effectively perceived to the left even though the second tone is presented to the right ear.

It is uncertain to what extent this 'lateral dominance' phenomenon affects auditory performance for MOC-CIS users. The described instability occurs for steady background sounds only. Furthermore, lateral dominance remains only until a sufficiently large change in the acoustic scene occurs. In the example of FIG. 13, the left ear dominates the binaural output in channel #7 only until the second tone pip, whose level is higher on the right ear, occurs. In realistic acoustic scenarios, the input to the two processors is far from steady, and hence lateral dominance is unlikely and may not be problematic.

Figures 14A, 14B, 14C:
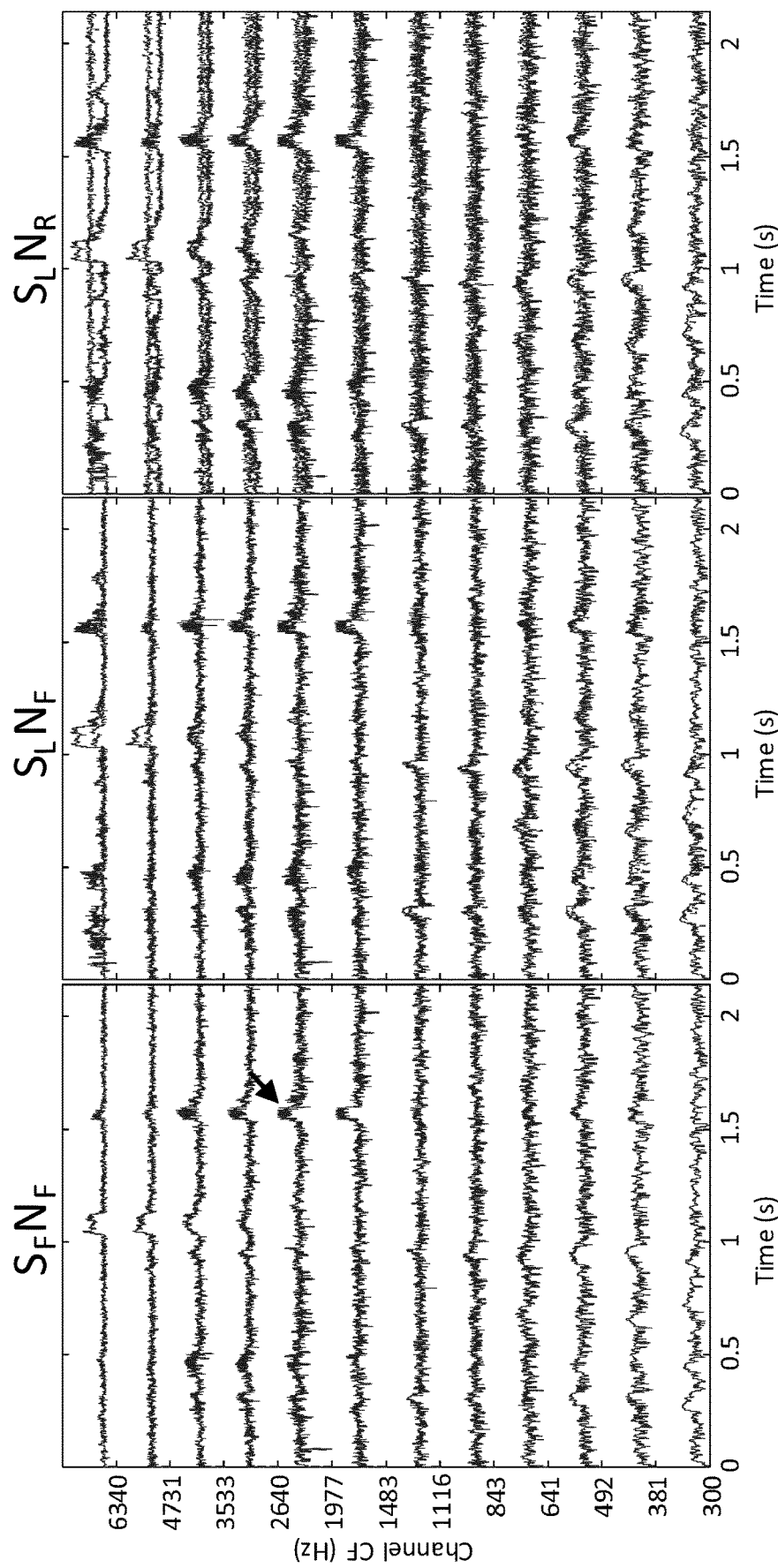
FIGS. 14a-14f. Show respective graphs of a comparison of channel outputs for two standard, stand-alone CIS processors (top) and two processors of the invention (bottom) for a Castilian-Spanish sentence in 0 dB SNR speech-shaped noise, for different relative locations of the tone and the noise: signal and noise in front of the listener (SFNF,left); signal to the left of the listener and noise in front of the listener (SLNF, middle); and signal to the left of the listener and noise to the right of the listener (SLNR, right). Signal level=Noise level=−6 dB. The same noise token (i.e., 'frozen' noise) was used in all cases. Each panel illustrates channel output amplitudes for the right-(red lines) and left-ear (blue lines) processors.
Figures 14D, 14E, 14F:
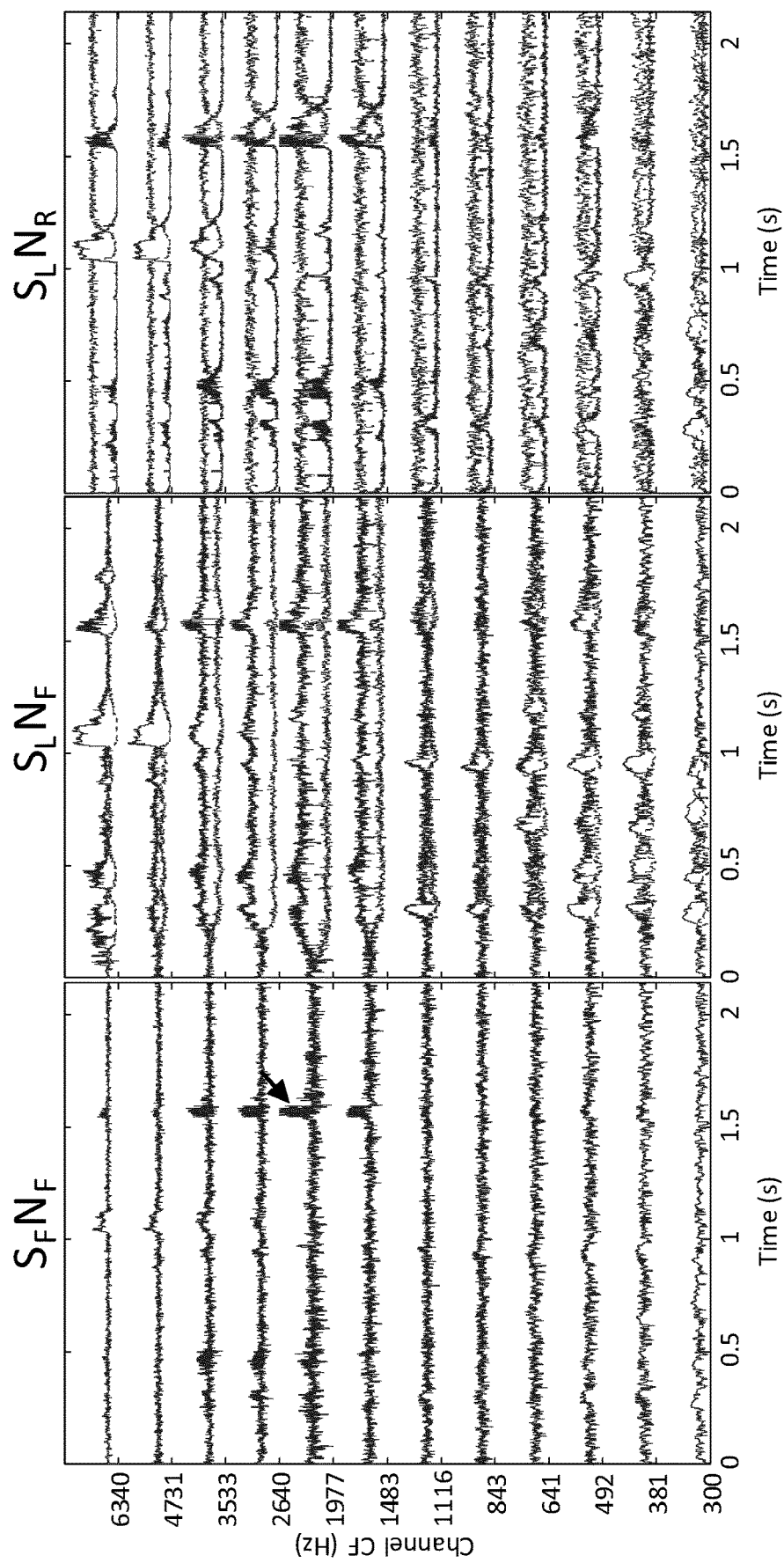

FIG. 14 illustrates channel outputs for a sentence of the Castilian-Spanish hearing-in-noise test (HINT). The sentence is "Yo tengo un coche verde" and is presented in speech-shaped noise. The speech level was −6 dB and the SNR was 0 dB. Let us first analyze the $S_FN_F$ condition (i.e., the left panels in FIG. 14). In this case, as expected, the output amplitudes are identical for the right-ear and left-ear for both the STD-CIS and MOC-CIS processors. Absolute amplitudes, however, are lower for the MOC-CIS (FIG. 13D) than for the STD-CIS (FIG. 13A) and amplitude modulation of the most salient speech features is deeper for the MOC-CIS than for the STD-CIS. This is better seen in FIG. 15, which shows a direct comparison of the right-ear output for the two processors for the feature indicated by the arrows in FIGS. 14A and 14D (channel #8). The baseline amplitude is lower for the MOC-CIS because identical stimuli reach the two ears and they inhibit each other by the identical amounts. As a result, the two MOC-CIS processors are operating more linearly than the two STD-CIS in this condition. The more linear functioning of the MOC-CIS processor, however, enhances amplitude modulation, which Let us now compare the channel outputs for the two processors for the $S_LN_F$ condition. Reasonably, for the STD-CIS processor (FIG. 14B), some speech features are above the noise floor and are more salient on the left—than on the right-ear processors because the speech was on the left. There is, nonetheless, significant overlap between the outputs for the left- and right-ear processors. The pattern of results for the MOC-CIS (FIG. 14E) is strikingly different. For channels #1 to #6 and #11-#12, the output on the right ear is inhibited by the most salient speech features, whose level is higher on the left than on the right ear as a result of the HRTF filtering. Therefore, for these channels, contralateral inhibition increases the IOD for the most salient speech features. HRTF filtering enhances mid-frequencies and the enhancement is comparatively greater for the left than for the right-ear because the speech was on the left. As a result, for mid-frequency channels (#7 to #10), the left ear inhibits the right ear much more than the other way around, causing the left-ear output dominate the binaural response overall. Despite this dominance, the most salient speech features are still present in the right-ear output, as shown by the arrows in FIG. 14E. In other words, the lateral dominance effect described in Sec. 3.1.4 occurs for these mid-frequency channels. Importantly, however, as shown above, output amplitudes in the left MOC-CIS processor never exceed those of the STD-CIS. Altogether, the present pattern of results suggests that the MOC-CIS should presumably enhance lateralization of the most salient speech features and simultaneously reduce the overall (binaural) noise level, particularly on the ear contralateral to the speech signal. This could enhance intelligibility and might reduce the listening effort.

Lastly, let us analyze the pattern of results for the $S_L N_R$ condition. The phenomena described above for the $S_L N_F$ condition also apply to this condition even more clearly. In the MOC-CIS (FIG. 14F), as a result of mutual contralateral inhibition, the speech features are clearly present in the output of the left-ear processor (the device facing the speech signal) while the noise is basically encoded in the output of the right-ear processor (the device facing the noise). Strikingly, there is little noise in the left-ear output. Furthermore, the output to the noise in the right ear is inhibited by the most-salient speech features in the left ear. Combined, the present results suggest that the MOC-CIS should presumably enhance lateralization of speech and noise, while increasing the IOD (i.e., reducing the contralateral noise level) to the most-salient speech features. This probably enhances spatial segregation and reduces listening effort.

Spatial location is a powerful cue for auditory streaming. More precisely, space is important for segregation of sequences of sounds interleaved in time but less important for separation of temporally overlapping (i.e., concurrent) sounds. It has been shown above that the MOC-CIS processor probably enhances the lateralization of spatially distant sounds, at least for signals (tones or speech) in broadband noise. This section is devoted to showing that the MOC-CIS may also enhance lateralization, hence speech segregation, in a multi-talker (e.g., cocktail party) situation.

Figure 16A:
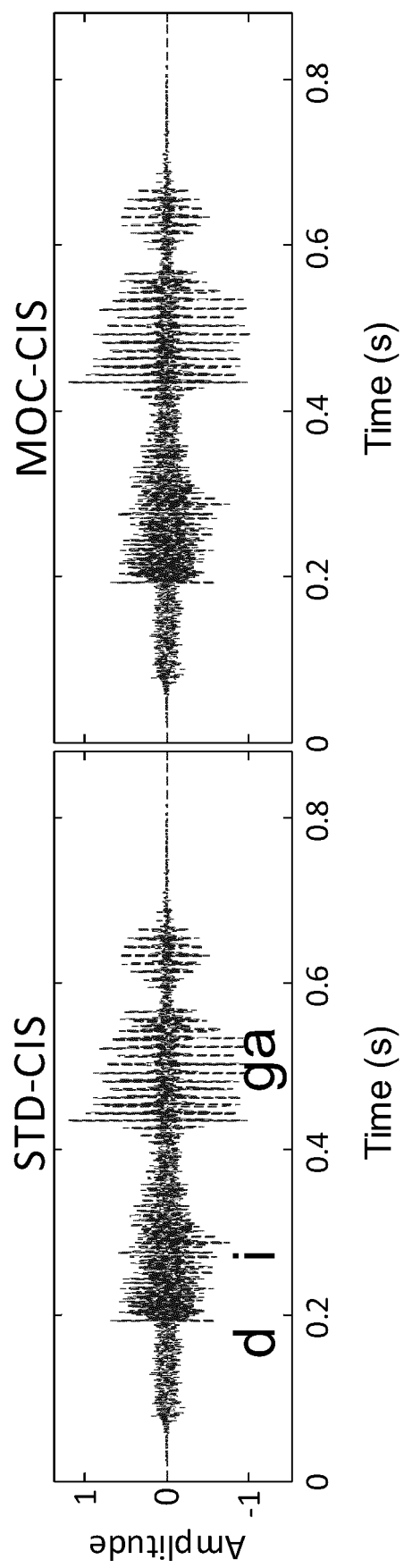
FIGS. 16a-16d. Show respective graphs of comparison of channel outputs for two standard, stand-alone CIS processors (left) and two processors of the invention (right) for two simultaneously presented Castilian-Spanish words: the word 'diga' was presented on the left ear, while the word 'sastre' was presented on the right ear. The two words had identical RMS levels of −15 dB.
Figure 16B:
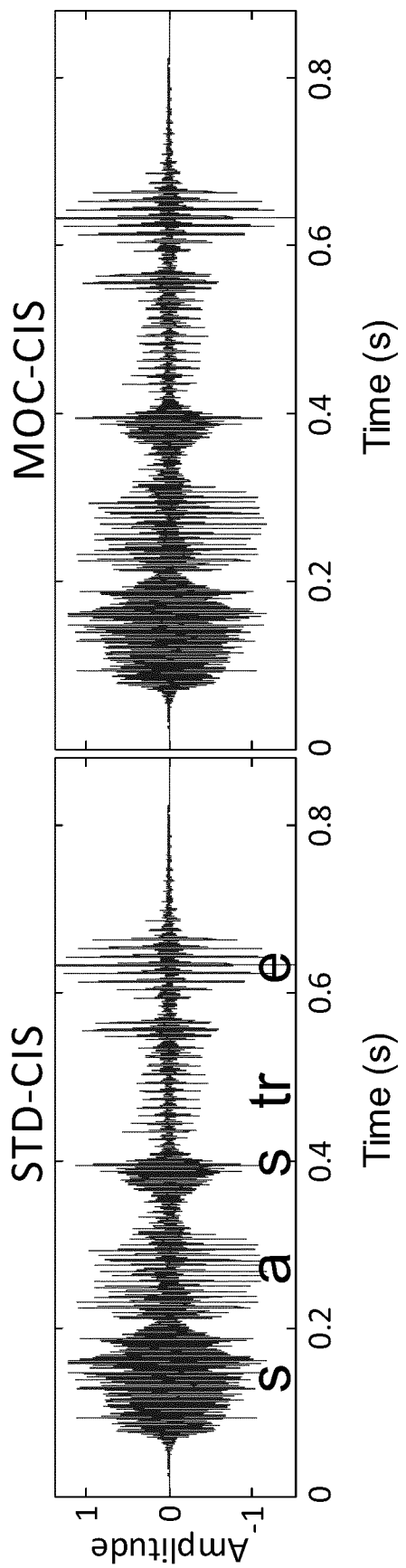

FIG. 16 shows channel outputs for bilateral STD-CIS and MOC-CIS processors for two different Castilian-Spanish words uttered simultaneously in the free field by speakers located on either side of the listener: the word ('diga') was uttered on the left side of the listener, and the word 'sastre' was uttered on the right side of the listener. The two words were disyllabic and were taken from a phonetically balanced speech audiometry set. In the present example, the two words were actually uttered by the same female speaker and were presented at the same level (−15 dB). Note that for this level that some clipping still occurred in the HRTF-filtered waveforms (i.e., the instantaneous amplitudes in FIGS. 16A and 16B sometimes exceeded ±1) but it was rare.

Figures 16C, 16D:
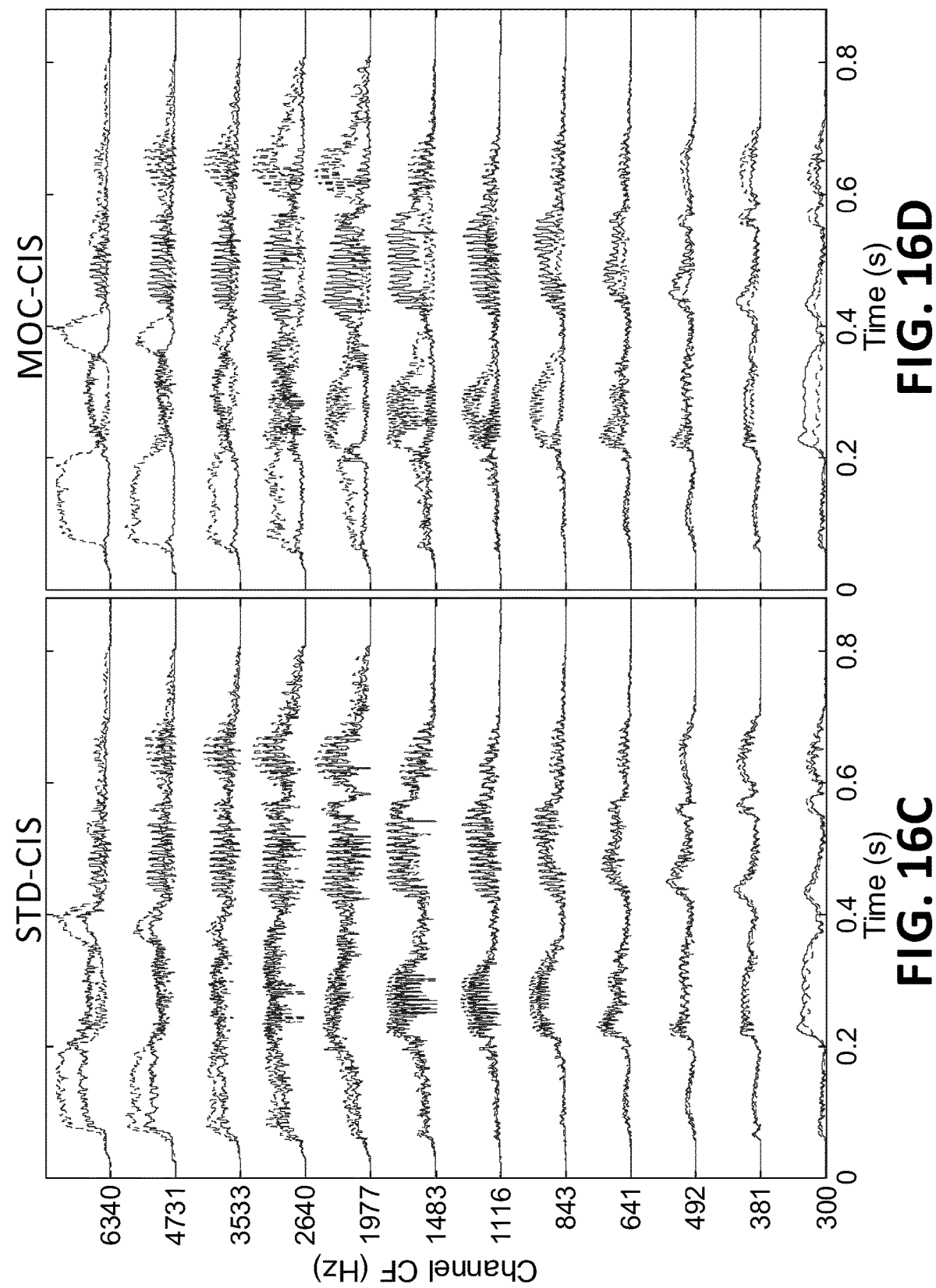

FIG. 16 shows that the left-right overlap between the words' most significant waveform features is much less for the MOC-CIS (FIG. 16D) than for STD-CIS (FIG. 16C). Indeed, compared to the STD-CIS, one can almost 'see' that the word diga, which was uttered on the left side of the listener, is encoded mostly in the left processor output, and the word sastre, which was uttered on the right side of the listener, is encoded mostly in the right processor output. This suggests that the MOC-CIS enhances lateralization, and possible spatial segregation, in situations with multiple spatially-distant speakers. This may enhance intelligibility in 'cocktail party' situations and reduce listening effort.

The results shown thus far were for a bilateral MOC-CIS processor where the compression parameter, c, was updated on a sample-by-sample basis; i.e., the rate of update was equal to the sampling frequency (44100 Hz). For high sampling frequencies, this could make the MOC-CIS too slow and impractical for actual use in bilateral CIs. On the other hand, given that channel envelopes were obtained by low-pass filtering with a cutoff frequency of 200 Hz, there may be no need to update c at a rate higher than twice this frequency. Indeed, MOC-CIS performance remained virtually unchanged for an update rate of 400 Hz (twice the cutoff frequency of the lowpass filters) if the compressed output was lowpass filtered again to minimize transient effects. The only significant difference with respect to the present results was an additional delay in the channel output waveforms introduced by this new back-end lowpass filter.

A typical implementation of the proposed bilateral MOC-CIS processor would require the listener to wear two CIs with corresponding sound processors capable of exchanging time-varying control signals and updating their frequency-specific compression maps adaptively in time. The exchange of control signals could be direct (i.e., from processor to processor) or indirect (from each processor to a remote control unit, to the contralateral processor). Communication between the components could be wired or wireless. As we have seen above, the rate of update of the control signals could be as fast as the sampling rate of the processors or as slow as twice the highest frequency in the channel envelopes (i.e., twice the frequency of the envelope detection low-pass filter).

Although bilateral cochlear implantation is becoming increasingly more frequent, particularly in children, the majority of current implant users still wear a single CI. The potential MOC-CIS benefits described here (e.g., noise reduction, increased modulation, and improved lateralization) are the result of bilateral sound processing rather than of bilateral electrical stimulation. Indeed, bilateral sound processing might still be useful for monaural CI users and it would not be hard to use a bilateral MOC-CIS with a single implant. Imagine, for instance, a single-sided CI user who wears a full system (implant+sound processor) in one ear and a processor-only (no implant) in the other ear. Alternatively, imagine a single-sided CI user whose single sound processor operates as if it was a bilateral with two different acoustic inputs, one from each ear (i.e., this would require a full CI in one ear plus a microphone in the non-implant ear). In these cases, it would still be possible to implement bilateral MOC-CIS processing and the pattern of electrical stimulation provided via the only available implant would preserve some of the argued benefits of bilateral processing.

Figure 15:
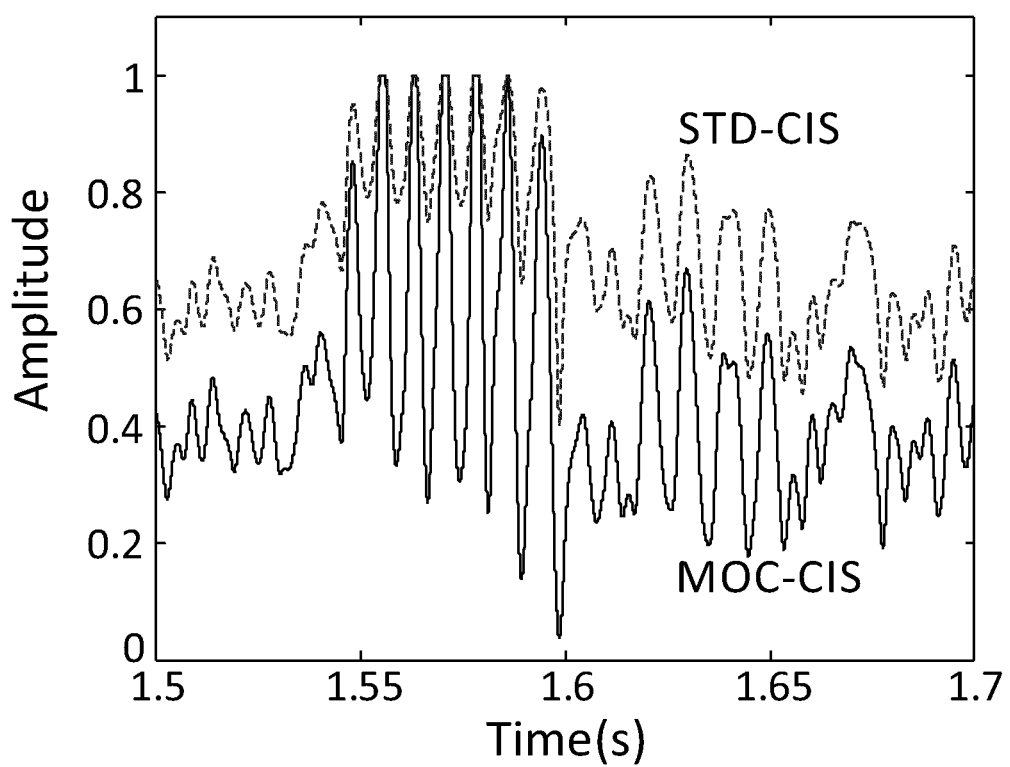
FIG. 15. Shows a graph of a comparison of MOC-CIS (top line) and STD-CIS (bottom line) right-ear output signals for channel #8. The fragments shown here are re-plotted from the data indicated by arrows in FIG. 13A and FIG. 13D.

In acoustic hearing, the ipsilateral and contralateral MOCR function simultaneously. Here, we have focused on contralateral MOCR effects as mimicked by the bilateral MOC-CIS. Incidentally, however, the MOC-CIS may also serve to mimic ipsilateral MOCR effects. To do it, it would be sufficient to use a bilateral MOC-CIS and assume diotic acoustic input, such as for the $S_F N_F$ condition described here. The present simulations suggest that the ipsilateral MOCR would reduce overall stimulation as compared to a STD-CIS (e.g., compare FIG. 10A with FIG. 10D) and would enhance amplitude modulation by linearization (FIG. 15).

The invention claimed is:

1. A sound enhancement method for cochlear implant sound processors for mimicking activating medial olivocochlear (MOC) efferents, the method comprising the steps of:
   capturing at least an acoustic signal by means of a microphone of a first of two interconnected sound processors,
   breaking down the acoustic signal into frequency bands, and
   respectively extracting an envelope for each signal in each frequency band,
   amplifying the envelope, by using a compression function, said amplification comprising in turn modifying a gain value of the amplification according to an energy of an output signal from a second of the two interconnected sound processors,
wherein the compression function is non-linear and is dynamically varying depending upon the energy of the output signal from the second processor, so that when the energy of the output signal from the second sound processor increases the compression function becomes more linear.

2. The method according to claim 1, wherein the energy of an output signal from the second sound processor is a time-weighted root-mean-square (RMS) amplitude over a preceding time period and the time-weighing is carried out by means of an exponentially decaying time-window.

3. The method according to claim 1, wherein the amplification uses an IBK mapping function.

4. The method according to claim 1, wherein the relationship between the gain value of amplification and the energy of an output signal of the other sound processor is a sigmoidal control function.

5. The method according to claim 1, wherein the sound processor capturing the acoustic sound signal further implements a coding strategy selected from the group consisting of CIS, ACE or SPEAK.

6. A sound enhancement device comprising two interconnected sound processors with respective microphones, the sound enhancement device characterised by at least one of the two sound processors being adapted to process an input acoustic signal, captured by its corresponding microphone, according to an output signal from the other processor, breaking down the acoustic signal into frequency bands, and extracting for each frequency band an envelope, wherein the sound processor capturing the acoustic signal is further configured to amplify the envelope extracted to obtain an amplified envelope, by using a compression function, the compression function being non-linear and dynamically varying depending upon the energy of the output signal from the second sound processor, so that when the energy of the output signal from the second sound processor increases, the compression function becomes more linear, thus modifying a gain value of the amplification according to an amplitude energy of an output signal of the second sound processor.

7. The sound enhancement device according to claim 6 wherein the sound processors are continuous interleaved sampling processors (CIS), Advanced Combination Encoder (ACE), or Spectral Peak (SPEAK).

8. The sound enhancement device according to claim 6 wherein the sound processors further comprise at last one filter selected from: Butterworth, Bessel, Chebichev, DRNL, and gammachirp.

9. The sound enhancement device according to claim 6 wherein the sound processors are adapted to amplify the input acoustic signal by means of a gain processing of said input acoustic signal with respect to an amplitude of an output signal of the processors.

10. A hearing aid characterized by comprising the sound enhancement device described in claim 6.

11. A sound enhancement device comprising at least one sound processor, with at least one microphone, emulating a multi-processor, sound enhancement device characterized by each of the emulated sound processors being adapted to process an input acoustic signal captured by the microphone, according by the output signal from other emulated sound processors, breaking down the acoustic signal into frequency bands, and extracting for each frequency band an envelope, wherein each of the emulated sound processors is further configured to amplify the envelope extracted to obtain an amplified envelope, being said amplification by using a compression function, the compression function being non-linear and dynamically varying, so that when the energy of the output signal from the second sound processor increases, the relationship between the compression function becomes more linear, thus, modifying a gain value of the amplification according to an amplitude energy of an output signal of the emulated sound processors.

12. The sound enhancement device according to claim 11 wherein the sound processors are continuous interleaved sampling processors (CIS), Advanced Combination Encoder (ACE), or Spectral Peak (SPEAK).

13. The sound enhancement device according to claim 11 wherein the sound processors further comprise at last one filter selected from: Butterworth, Bessel, Chebichev, DRNL, and gammachirp.

14. The sound enhancement device according to claim 11 wherein the sound processors are adapted to amplify the input acoustic signal by means of a gain processing of said input acoustic signal with respect to an amplitude of an output signal of the processors.

15. A hearing aid characterized by comprising the sound enhancement device described in claim 11.

* * * * *